: 6,120,433
: Sep. 19, 2000

United States Patent
Mizuno et al.

[54] SURGICAL MANIPULATOR SYSTEM

[75] Inventors: Hitoshi Mizuno; Toshimasa Kawai; Nobuyuki Dohguchi, all of Tokyo, Japan

[73] Assignee: Olympus Optical Co., Ltd., Tokyo, Japan

[21] Appl. No.: 08/950,213

[22] Filed: Oct. 14, 1997

Related U.S. Application Data

[63] Continuation of application No. 08/448,724, May 25, 1995, abandoned.

[30] Foreign Application Priority Data

Sep. 1, 1994 [JP] Japan .................................. 6-208887
Oct. 25, 1994 [JP] Japan .................................. 6-260285

[51] Int. Cl.[7] .............................. A61B 1/00; A61B 19/00
[52] U.S. Cl. ..................... 600/102; 600/118; 606/130
[58] Field of Search ........................... 600/101, 102, 600/117, 118; 606/130, 1; 395/92, 99, 85; 901/2, 47; 709/208

[56] References Cited

U.S. PATENT DOCUMENTS

| | | | |
|---|---|---|---|
| 3,923,166 | 12/1975 | Fletcher et al. ............................. | 414/4 |
| 4,604,016 | 8/1986 | Joyce ......................................... | 414/7 |
| 5,005,559 | 4/1991 | Blanco et al. ........................... | 600/114 |
| 5,217,003 | 6/1993 | Wilk . | |
| 5,351,676 | 10/1994 | Putman .................................. | 600/117 |
| 5,408,409 | 4/1995 | Glassman et al. ................. | 364/413.13 |
| 5,410,638 | 4/1995 | Colgate et al. ............................ | 395/99 |
| 5,417,210 | 5/1995 | Funda et al. .......................... | 128/653.1 |
| 5,524,180 | 6/1996 | Wang et al. ............................ | 600/118 |
| 5,540,649 | 7/1996 | Bonnell et al. ........................ | 600/114 |
| 5,545,120 | 8/1996 | Chen et al. ............................. | 600/117 |
| 5,876,325 | 3/1999 | Mizuno et al. ........................ | 600/117 |
| 5,878,193 | 3/1999 | Wang et al. ............................ | 600/117 |

FOREIGN PATENT DOCUMENTS

| | | |
|---|---|---|
| 63-296746 | 12/1988 | Japan . |
| 3-121064 | 5/1991 | Japan . |
| 5-253246 | 10/1993 | Japan . |
| 6-113997 | 4/1994 | Japan . |

OTHER PUBLICATIONS

"Virtual Surgery", *Discovery*, Dec. 1994.
"Teleoperator Control Using Telepresence", International Encyclopedia of Robotics.

*Primary Examiner*—John P. Leubecker
*Attorney, Agent, or Firm*—Frishauf, Holtz, Goodman, Langer & Chick, P.C.

[57] ABSTRACT

A surgical manipulator system comprising an operation device, a slave manipulator, a medical device, and a controller. The operation device is located in a region to be operated by a surgeon. The slave manipulator can have access into a surgery region. The medical device is held by the slave manipulator and can be moved a body cavity. The controller can operate in a first mode to move the slave manipulator or the medical device, or both, such that the axis of the medical device passes a fulcrum fixed in a space even before the medical device is inserted into the body cavity.

36 Claims, 18 Drawing Sheets

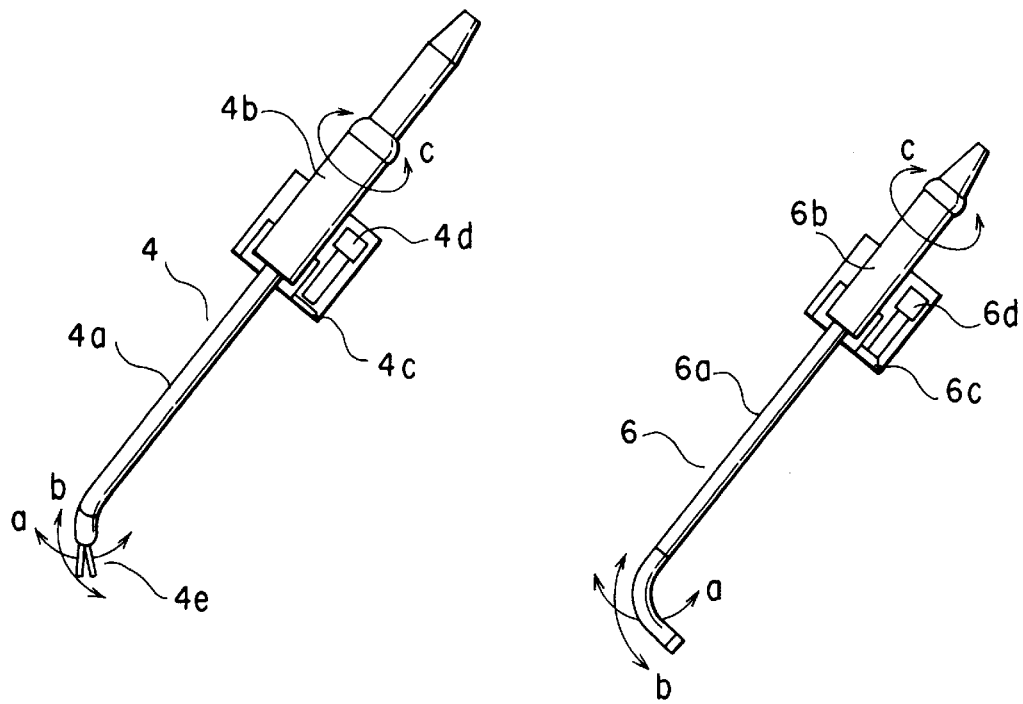
F I G. 1A    F I G. 1B
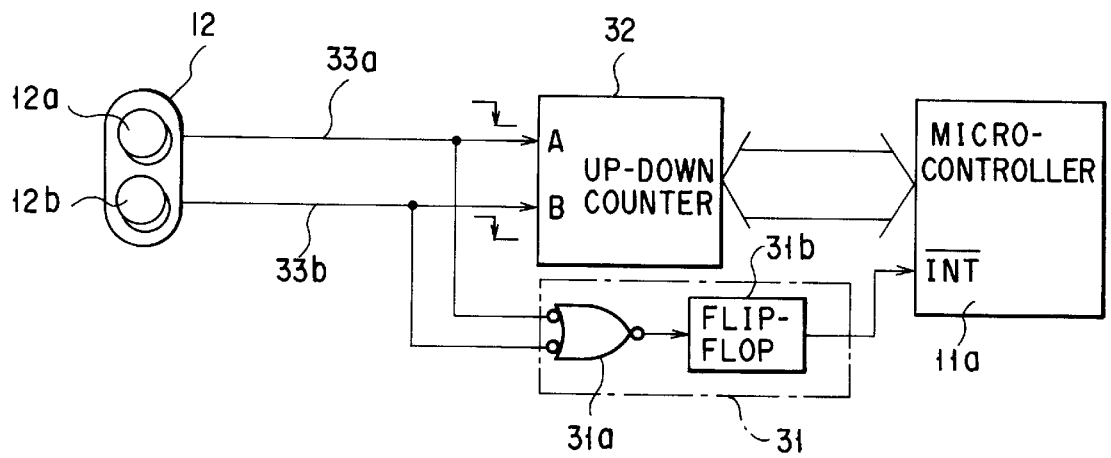
F I G. 3

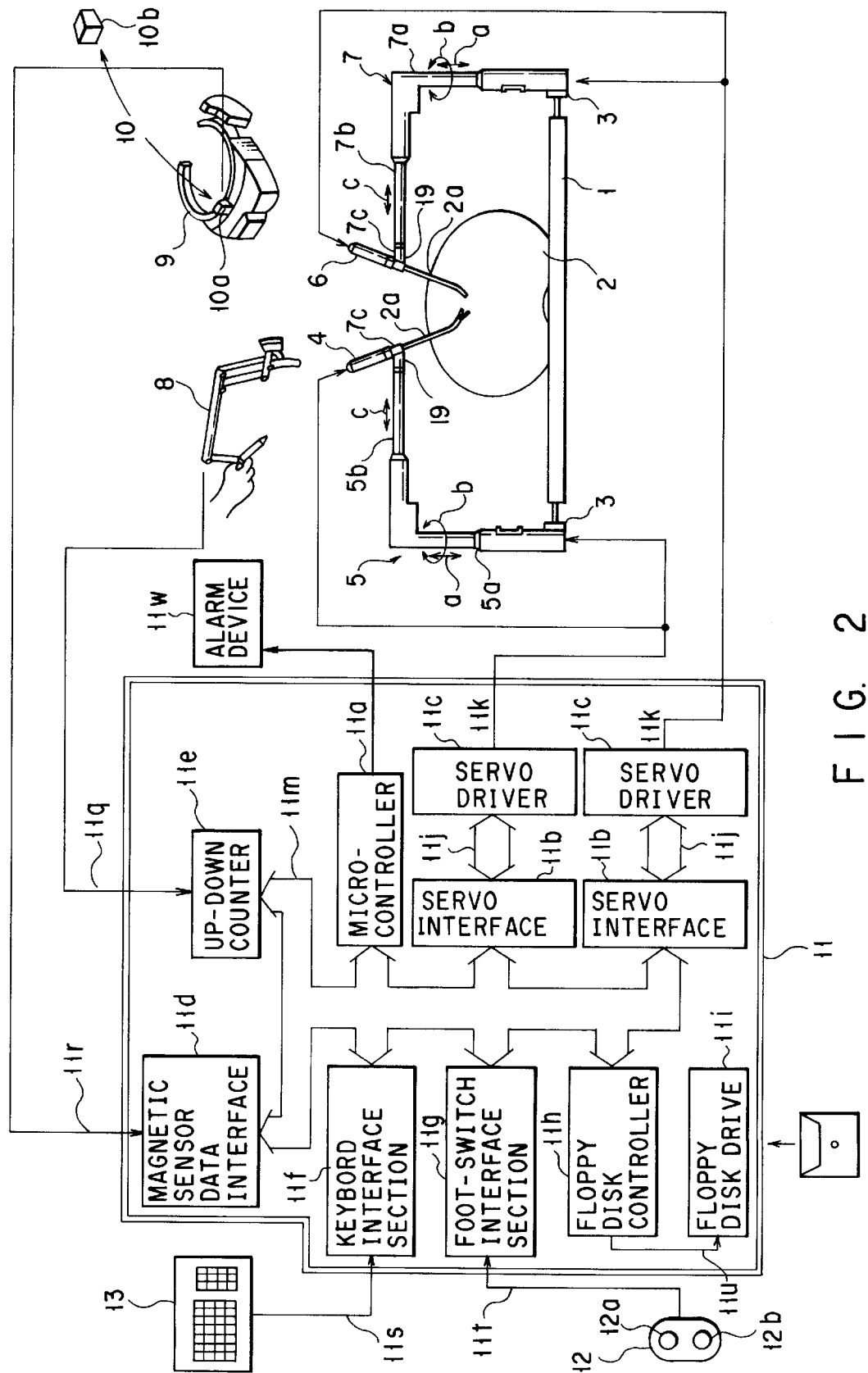
F I G. 2

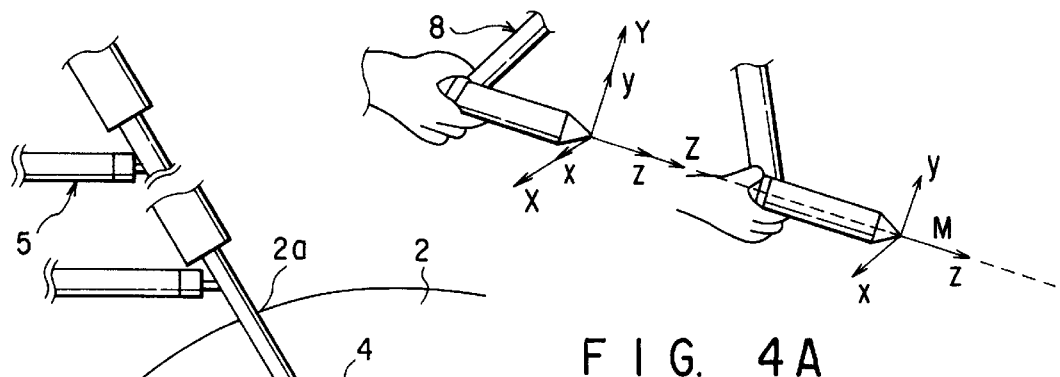
FIG. 4A
FIG. 4B
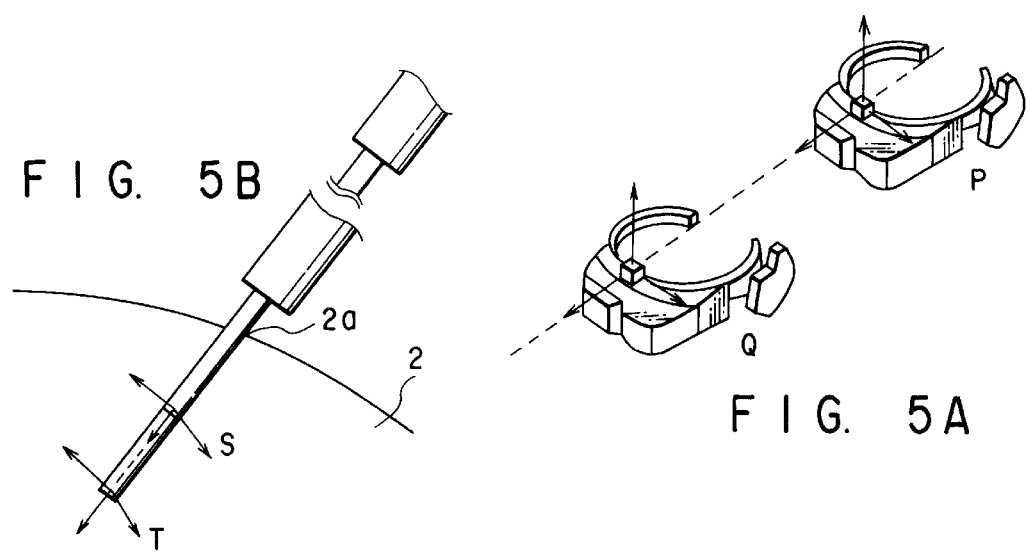
FIG. 5B
FIG. 5A
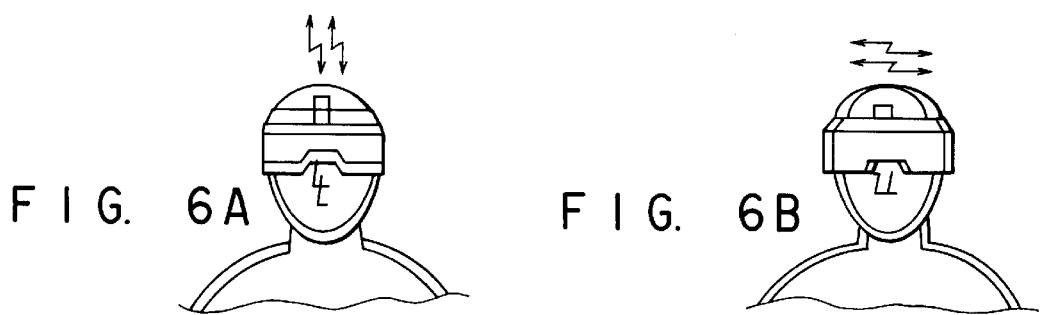
FIG. 6A
FIG. 6B

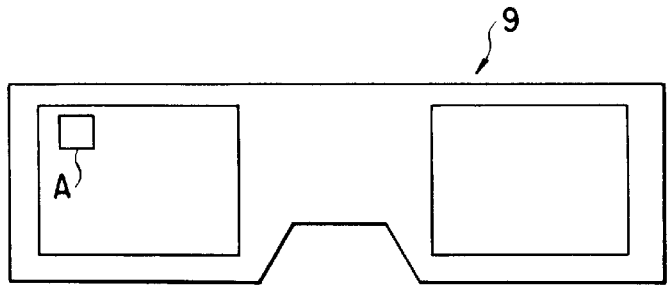
FIG. 7A
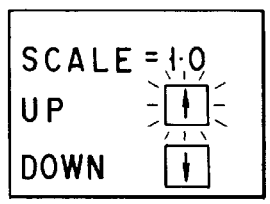
FIG. 7B
1. MASTER-SLAVE MODE
2. INSTRUCTION MODE
3. PLAYBACK MODE
4. RETURN-TO-ORIGIN MODE
5. END
FIG. 7C
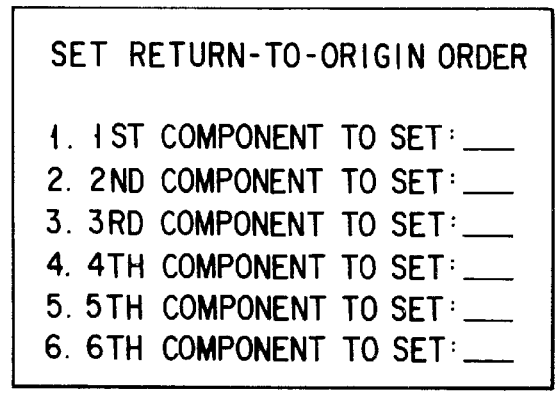
FIG. 7D
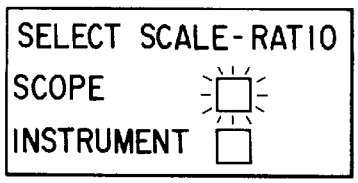
FIG. 7E
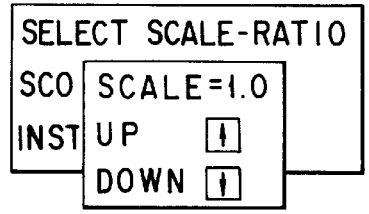
FIG. 7F

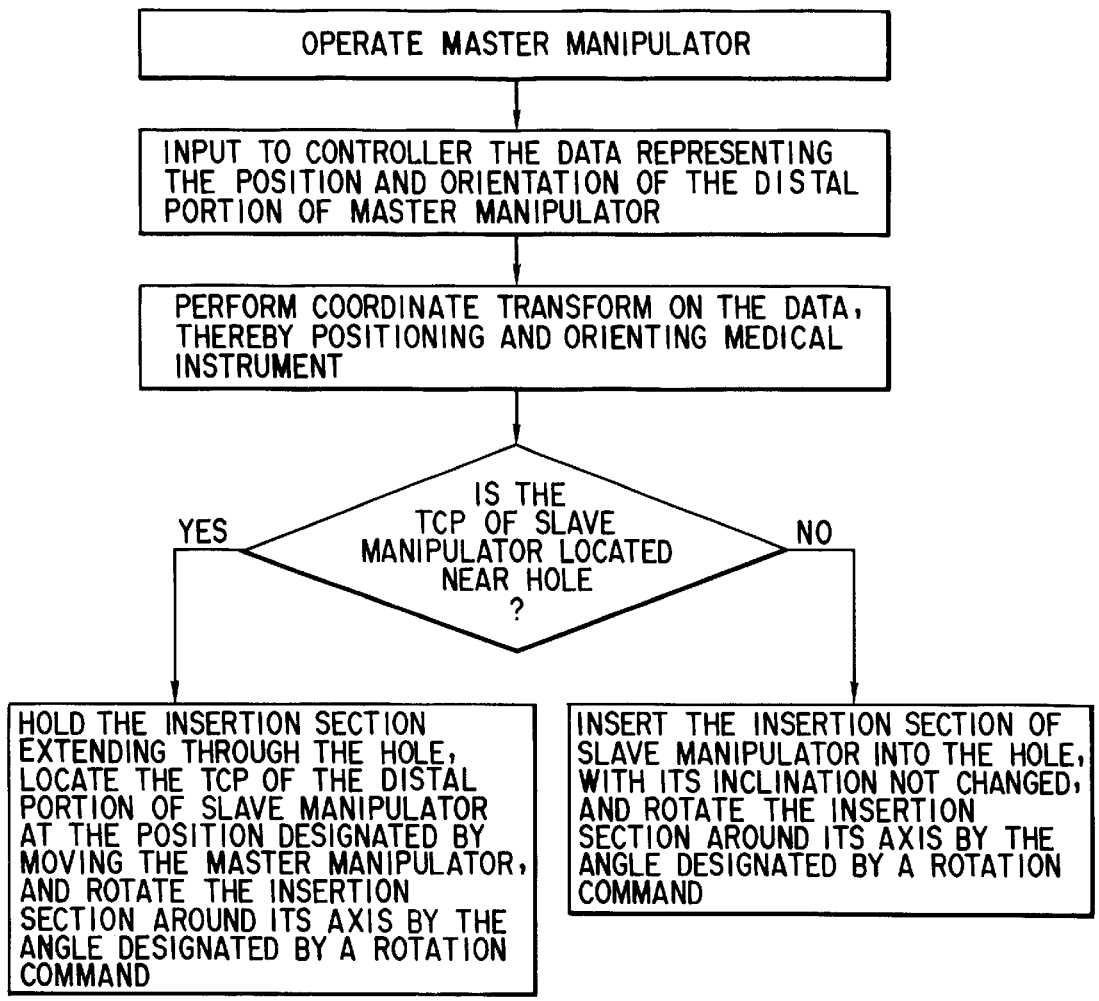
F I G. 14

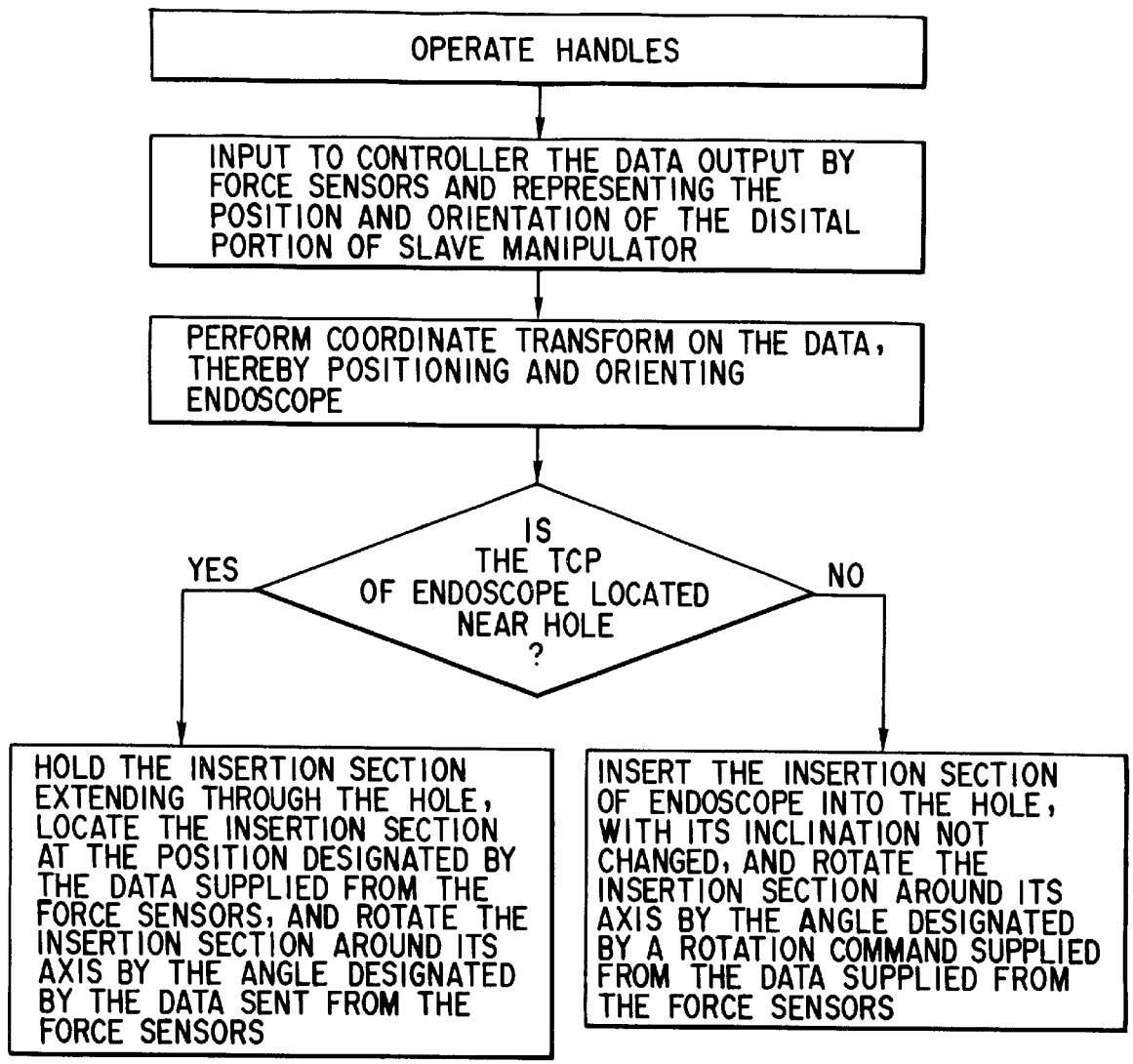
F I G. 17

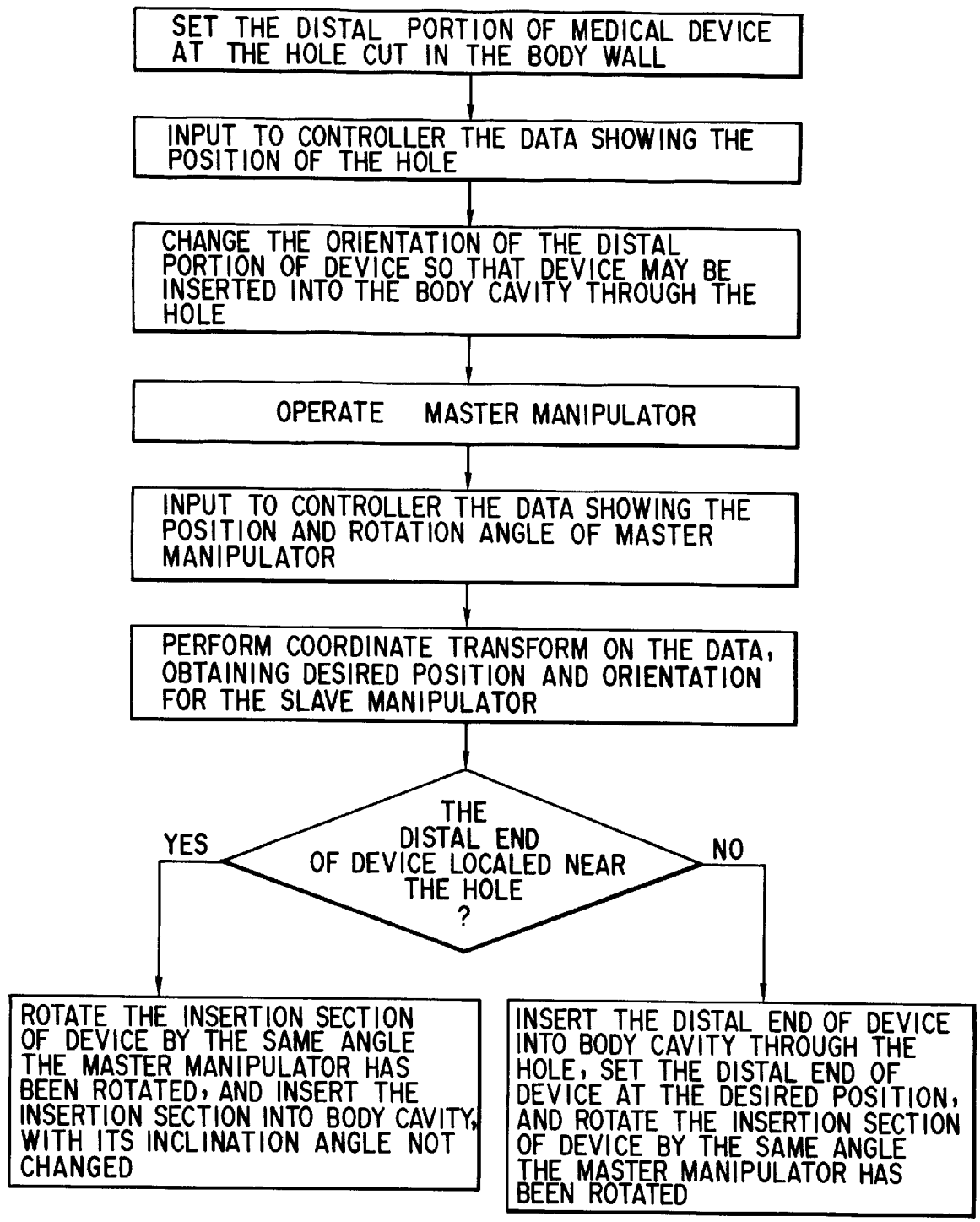
F I G. 25

SURGICAL MANIPULATOR SYSTEM

This application is a Continuation of application Ser. No. 08/448,724, filed May 25, 1995 now abandoned.

BACKGROUND OF THE INVENTION

1. Field of the Invention

The present invention relates to a surgical manipulator system which is designed to insert a medical device such as an endoscope into a body cavity of a subject for the purpose of examining the interior of the cavity and performing surgery within the cavity.

2. Description of the Related Art

Hitherto, transcutaneous endoscope surgery in which an endoscope or a medical instrument is inserted into a body cavity through a hole cut in the body wall (e.g., the abdominal wall) to perform various treatments in the body cavity has been known. This is because transcutaneous endoscope surgery involves no large-scale incision and is therefore scarcely invasive to the patient. This type of surgery is now widely performed to extract the gallbladder or a part of either lung.

A surgical manipulator is known which holds an endoscope or a medical instrument and which a surgeon can remote-control to manipulate the endoscope or the instrument in performing a surgical operation. A surgical manipulator of this type has manipulators and an insertion section for holding an endoscope or a medical instrument. The insertion section is a multi-joint structure, having a plurality of rods joined together. The actuators drive the rods, respectively, so that the insertion section may smoothly approach an object within a body cavity.

To perform a successful endoscope surgery, it is desirable that the endoscope or the instrument inserted in the body cavity be manipulated in a space as broad as possible. The endoscope or the instrument can be so manipulated by the use of a manipulator with a multi-joint insertion section which has a high degree of freedom. For example, the master-slave surgical manipulator system disclosed in Jpn. Pat. Application 6-131810 may be used to set an endoscope and a medical instrument at a desired position and orientation within a body cavity.

The master-slave manipulator system comprises a slave section and a master section. The slave section comprises a scope manipulator holding an endoscope and an instrument manipulator holding a medical instrument. The master section comprises a head-mount display and a master arm. To perform an endoscope surgical operation, a surgeon wears the head-mount display and holds the master arm. As the surgeon operates the master arm, the instrument manipulator is moved in the same way as the master arm. As he or she moves the head, the scope manipulator is moved in the same manner as the surgeon's head. Thus, the surgeon can carry out an endoscope surgical operation in the same way he or she would perform laparotomy.

Needless to say, the distance and speed the master arm and the head-mount display are moved totally depend on the surgeon's habit. Preset in the surgical manipulator system described above are fixed control parameters, such as a scale ratio between the moving amounts of the master arm (or the head-mount display) and those of the slave arms (i.e., the scope manipulator and the instrument manipulator) and the response of the slave arms to the motion of the master arm (or the head-mount display). Inevitably, the surgeon needs to be trained to operate the master arm such that the slave arm would move in the very way he or she wants. Unless the surgeon is so trained, it will take him or her much time to perform an endoscope surgical operation by using the surgical manipulator system.

It is desired that an endoscope and a medical instrument, either held by a slave manipulator, be inserted into a body cavity through the holes cut in the body wall and be moved within the body cavity, without applying an excessive force at the holes. To this end, the endoscope may be held by a scope holder of the type disclosed in, for example, Japanese Patent Application 4-221571. The scope holder is designed to hold an endoscope at an appropriate position with respect to the hole cut in the body wall, while the endoscope is being inserted through the hole into the body cavity.

Japanese Patent Application 62-134503 discloses an apparatus which controls a microscope holder by mechanical means, so that the focal point of the surgical microscope may be located at the specified point on the patient's head throughout stereotactic surgery. Japanese Patent Application 1-257907 discloses an apparatus which is used in combination with an X-ray CT scanner and which can orient a medical instrument to the center of an imaginary spherical surface which surrounds the object of stereotactic surgery. Japanese Patent Application 4-51778 discloses an apparatus designed to position a microscope in an imaginary spherical surface which surrounds the object of stereotactic surgery such that the focal point of the microscope is placed at the object.

The scope holder disclosed in Japanese Patent Application 4-221571 must be mechanically adjusted to allow the endoscope to pass through the hole made in the body wall. The mechanical adjustment required is cumbersome. Further, the link mechanism, which is used to guide the endoscope through the hole into and out of the body cavity, has a complex structure and occupies a large space.

The apparatus disclosed in Japanese Patent Application 62-134503 is difficult to operate since it must be mechanically adjusted, too, to locate the focal point of the surgical microscope at the specified point on the patient's head. The link mechanism, which is employed to locate the focal point, is complicated in structure and is large in size, occupying a large space.

The apparatus disclosed in Japanese Patent Application 1-257907 also require mechanical adjustment in order to orient a medical instrument to the center of the object of stereotactic surgery. This mechanical adjustment is complex. Further, the link mechanism, used to orient the instrument, has a complicated structure and occupies a large space.

The apparatus disclosed in Japanese Patent Application 4-51778 has electric motors which are controlled to place the focal point of the microscope at a specified point on the object of stereotactic surgery. The application, however, does not teach how to translate the movement of a joystick into the control of the motors.

SUMMARY OF THE INVENTION

The first object of the present invention is to provide a surgical manipulator system which can be operated easily.

The second object of the invention is to provide a surgical manipulator system which can guide a medical instrument into and out of a body cavity through a hole cut in the body wall, without applying an excessive force at that hole, and which can hold the instrument at an object of surgery within the body cavity.

To attain the objects of the invention, according to the invention there is provided a surgical manipulator system which comprises: operation means located in a region to be operated by a surgeon; a slave manipulator located to make access into a surgery region; a medical device held by the slave manipulator and movable into a body cavity; and control means for moving at least one of the slave manipulator and the medical instrument in the same way as the master manipulator is moved.

The control means has three control modes. In the first control mode, the control means moves the slave manipulator or the medical device, or both, such that the longitudinal axis of the instrument passes a fulcrum located in a space. In the second control mode, the control means moves the slave manipulator or the medical device, or both, such that the longitudinal axis of the device is kept inclined at a specific angle as long as a fulcrum at a hole which is cut in a body wall and through which the distal portion of the device is inserted into the body cavity. In the third control mode, the control means moves the slave manipulator or the medical device, or both, such that the longitudinal axis of the instrument passes a fulcrum, allowing the distal portion of the device to move in a straight line.

Furthermore, the control means moves the slave manipulator in the same way as the operation means is moved, in accordance with data supplied from means which changes control parameters required to control the slave manipulator or the medical device, or both.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1A shows a medical instrument attached to the instrument arm 5 of a surgical manipulator system which is a first embodiment of the invention;

FIG. 1B illustrates a scope attached to the scope arm 7 of the surgical manipulator system;

FIG. 2 is a diagram showing the surgical manipulator system according to the first embodiment;

FIG. 3 is a circuit diagram for explaining how a signal is processed while being supplied from the foot switch unit to the micro-controller, both incorporated in the system;

FIG. 4A is a diagram explaining how a surgeon moves the master arm of the system;

FIG. 4B is a diagram explaining how the instrument arm is moved as the surgeon moves the master arm;

FIG. 5A is a diagram explaining how the HMD which the surgeon wears moves;

FIG. 5B is a diagram explaining how the scope is moved as the HMD is moved;

FIG. 6A is a diagram showing how the surgeon's head moves up and down;

FIG. 6B is a diagram showing how the surgeon's head moves sideways;

FIGS. 7A to 7F are diagrams for explaining how the control parameters are changed;

FIG. 14 is a flow chart for explaining the operation of the system shown in FIG. 9;

FIG. 17 is a flow chart for explaining the operation of the surgical manipulator system illustrated in FIG. 9;

FIG. 25 is a flow chart for explaining the operation of a surgical manipulator system which is a twelfth embodiment of the present invention.

DETAILED DESCRIPTION OF THE PREFERRED EMBODIMENTS

Figure 8A:
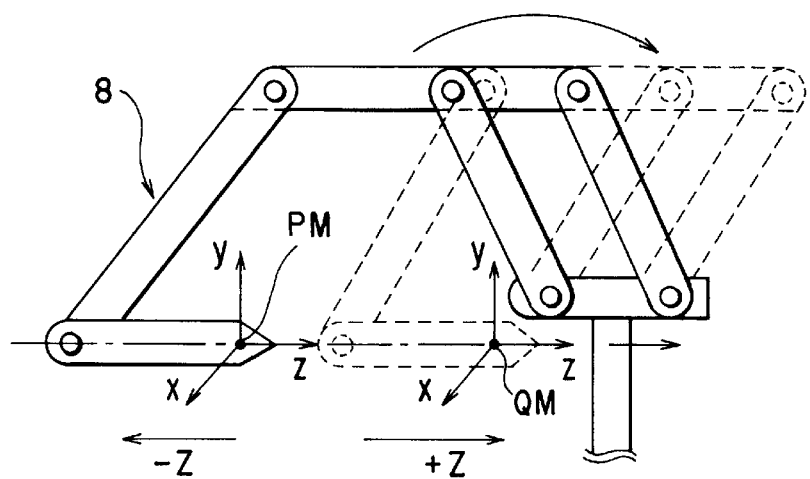
FIG. 8A is a diagram showing the mechanism incorporated in either slave manipulator, explaining how the slave manipulator can be driven, despite the mechanical restriction of the master arm.

Embodiments of the invention will be described below, with reference to the accompanying drawings.

FIG. 2 shows a surgical manipulator system according to the first embodiment of the invention. Illustrated in FIG. 2 are an operating table 1 and a patient 2 laying on the table 1. The operating table 1 has two side rails 3, each at one side. An instrument arm 5 and a scope arm 7 are removably connected to the side rails 3, respectively. The instrument arm 5 and scope arm 7 are provided for positioning a medical instrument 4 and a scope 6, respectively, in a body cavity of patient 2. The instrument 4 and the scope 6 are inserted into the body cavity through holes 2a cut in the patient's body wall.

The instrument arm 5 has a free-joint mechanism 19 which holds the medical instrument 4. Similarly, the scope arm 7 has a free-joint mechanism 19 which holds the scope 6. Either free-joint mechanism 19 has a plurality of freedom degrees and can move so as to apply no excessive force at the hole 2a when the hole 2a moves as the patient 2 moves while undergoing the operation.

Both the instrument arm 5 and the scope arm 7 can expand and contract in the vertical direction indicated by arrow a, can rotate in the direction of arrow b, and can expand and contract in the horizontal direction indicated by arrow c—as is illustrated in FIG. 2. Each arm incorporates actuators (not shown), which enables the arm to expand, contract and rotate in this manner. The actuators are servo motors of the type which are used in industrial robots.

As shown in FIGS. 1A, 1B, the medical instrument 4 attached to the distal end of the instrument arm 5 has an insertion section 4a, and the scope 6 attached to the distal end of the scope arm 7 has an insertion section 6a. The insertion sections 4a and 6a have a distal portion each, which can be bent in two directions a and b indicated in FIGS. 1A, 1B. The distal portion of the insertion section 4a is bent in either direction when the servo motor (not shown) provided in the motor housing 4b of the instrument 4 is rotated, driving a wire (not shown, either) which extends through the insertion section 4a. Similarly, the distal portion of the insertion section 6a is bent in either direction when the servo motor (not shown) provided in the motor housing 6b of the scope 6 is rotated, driving a wire (not shown, either) which extends through the insertion section 6a.

As shown in FIGS. 1A, 1B, the free-joint mechanisms 19 have the free-joint sections 4c and 6c, respectively. The sections 4c and 6c incorporate servo motors 4d and 6d and rotary mechanisms. The rotary mechanisms are operated when the servo motors 4d and 6d are driven, whereby the instrument 4 and the scope 6 are rotated in the direction of arrow c. The instrument 4 has a forceps 4e at its distal end and a forceps-driving mechanism (not shown) located in its distal end. The forceps-driving mechanism opens and close the forceps 4e when driven by a rod or a wire which is pushed and pulled by a servo motor (not shown) provided in the motor housing 4b of the instrument 4.

The medical instrument 4 and the instrument arm 5 constitute an instrument slave manipulator. The scope 6 and the scope arm 7 constitute a scope slave manipulator.

The surgical manipulator system further comprises a master arm 8 and a head-mount display 9 (hereinafter referred to as "HMD"), as is shown in FIG. 2, which form an operation means. The master arm 8 is input means for the instrument slave manipulator, and the HMD 9 is input means for the scope slave manipulator.

The master arm 8 has a plurality of link mechanisms, each comprising one link. The link of each link mechanism has an encoder (not shown) mounted on it. The encoder detects the movement of the link and generates a signal representing the distance the link is moved. Hence, the distance the master arm 8 is moved is determined from the signals output from the encoders mounted on the links of the master arm 8.

Each link of the master arm 8 has an electromagnetic clutch (not shown). The clutches cooperate to prevent the master arm 8 from moving downwards by its own weight when the surgeon releases the master arm 8. That is, the electromagnetic clutches keep holding the master arm 8 unless the surgeon moves the arm 8. To drive the master arm 8 by setting the surgical manipulator system in master-slave mode, the surgeon operates a foot switch unit 12, thereby to control the electromagnetic clutches. In other words, the foot switch unit 12 is operated to lock and release the master arm 8. Thus, while the system is set in the master-slave mode, the movement of the master arm 8 can be transmitted to the instrument slave manipulator, whereby the instrument slave manipulator can move in the same way as the surgeon manipulates the master arm 8.

The signals output from the encoders mounted on the links of the master arm 8 are used to operate the instrument slave manipulator. In place of the master arm 8, a three-dimensional joystick having strain gauges or pressure sensors or a position-recognizing device such as a force sensor may be used to generate information required for operating the instrument slave manipulator. The joystick and the device are more simple than the master arm 8 in terms of structure.

The HMD 9 has a screen (not shown) for presenting an image which the scope 6 is scanning. The screen is located in front of the surgeon's eyes who wears the HMD 9. The surgeon can therefore observe the image however his or her head moves. Thus, the surgeon need not be bothered to turn his or her head to see the image on a TV monitor as in the case where the image is displayed by a TV monitor installed in the operating room. In other words, the surgeon keeps watching the image as long as he or she wears the HMD 9 unless he or she shuts his or her eyes. This enables the surgeon to carry out the surgery in safety.

The distance the surgeon's head moves in a space is detected by a magnetic sensor 10. The magnetic sensor 10 comprises a magnetism-generating section 10b and a magnetism-detecting section 10a. The section 10b generates a magnetic field of uniform intensity, and the section 10a detects the magnetic field. The magnetism-detecting section 10a is mounted on the substantially central portion of the HMD 9.

How the magnetic sensor 10 detects the motion of the surgeon's head will be explained in brief. The magnetism-sensing section 10a detects changes in the magnetic field which have occurred as the surgeon moves the head. The information representing these changes is processed to provide Eulerian angles (roll, pitch and yaw) which represent the distance the section 10a has moved from the section 10b and the inclination the section 10b assumes with respect to the section 10a. From the Eulerian angles there are determined the movement and inclination of the surgeon's head.

The magnetic sensor 10 may be replaced by an ultrasonic sensor, which can serve to detect the movement of the surgeon's head. Alternatively, a solid-state imaging device such as a CCD may be arranged so as to generate image data showing the surgeon's head, and the image data may be processed to determine the movement of the head.

The surgical manipulator system has a controller 11 to control both the instrument slave manipulator and the scope slave manipulator. As shown in FIG. 2, the controller 11 comprises several function modules required for operating the slave manipulators. The function modules are: a micro-controller 11a, two servo interfaces 11b, two servo drivers 11c, a magnetic sensor data interface circuit 11d, an up-down counter 11e, a keyboard interface section 11f, a foot switch interface section 11g, a floppy disk drive 11i, and a floppy disk controller 11h. The micro-controller 11a is a CPU for controlling all other function modules. The up-down counter 11e stores the data generated by the encoders mounted on the master arm 8 and representing the distance the master arm 8 has been moved. The counter 11*e* has input ports in the same number as the encoders on the master arm 8. To be more specific, the up-down counter 11*e* increases or decreases the initial count set when the power switch to the controller 11 is closed, in accordance with the signals output from the encoders.

The magnetic sensor data interface circuit 11*d* receives the information supplied from the magnetism-detecting section 10*a* mounted on the HMD 9, namely the data representing the absolute position of the magnetic sensor 10 and the data representing the Eulerian angles. The keyboard interface section 11*f* receives the information input by operating a keyboard 13.

The floppy disk drive 11*i* is provided to record on a floppy disk the information for controlling both slave manipulators. The floppy disk controller 11*h* is used to control the floppy disk drive 11*i*. Included in the information recorded on the floppy disk are data for controlling the scope slave manipulator and the instrument slave manipulator and control parameters such as the scale ratio between the moving amount of the master arm 8 (or HMD 9) and those of the instrument arm 5 (or scope arm 7). Needless to say, the floppy disk can be replaced by a hard disk or a optomagnetic disk which is commonly used in the peripheral devices to a data-processing apparatus. Alternatively, the floppy disk may be replaced by an EEPROM of low element level or a RAM having a back-up battery.

The foot switch interface section 11*g* receives the information generated by operating the foot switch unit 12. The section 11*g* is a circuit which has the structure illustrated in FIG. 3. With reference to FIG. 3, it will be explained how the section 11*g* operates.

As shown in FIG. 3, the foot switch unit 12 has two foot switches 12*a* and 12*b*. As long as the foot switch 12*a* remains not trod upon, the signal line 33*a* stays at high potential. When the surgeon treads on the foot switch 12*a*, the signal line 33*a* is set at low potential. A low-level signal is thereby input to a wired OR circuit 31*a*. As a result, the output of a flip-flop 31*b* changes, and a signal is input to the interrupt terminal INT of the micro-controller 11*a*.

When either foot switch 12*a* of the foot switch unit 12 is trod on for the first time after the power switch of the controller 11 has been closed, the INT signal line is set at high potential. When the foot switch 12 is trod on thereafter, the interrupt terminal INT is set at low potential, whereby the operation in the micro-controller 11*a* jumps to an interrupt routine. If the master-slave mode is set or released in accordance with the number of times the foot switch 12 is trod on, the operation does not jump to the interrupt routine when the foot switch 12 is trod upon. Rather, the micro-controller 11*a* determines whether the master-slave mode should be set or not in accordance with the number of interrupts made and the timing of changes in the signal at the interrupt terminal INT.

In the present embodiment, the master-slave mode is set when either foot switch 12 is trod once, and is released when the foot switch 12 is trod again. This is achieved by a toggle switch 31 incorporated in the foot switch interface section 11*g*. As seen from FIG. 3, the toggle switch 31 comprises the wired OR circuit 31*a* and the flip-flop 31*b*. The interface section 11*g* has an up-down counter 32 which counts the number of times the foot switch 12 is trod upon. The number of times thus counted will be applied to alter the control parameters. The count of the up-down counter 32 increases by one every time the switch 12*a* is trod upon, and decreases by one every time the switch 12*b* is trod upon. When the foot switch 12 is operated, setting the master-slave mode, the electromagnetic clutches on the master arm 8 are released, allowing the surgeon to move the master arm 8 freely. The foot switch 12*a* is used to set or release the master-slave mode in the present embodiment. Instead, a switch may be provided on the master arm 8, near the grip portion thereof, and the surgeon may operate this switch by hand, thereby to set or release the master-slave mode.

As can be understood from FIG. 2, the first servo interface 11*b* is provided to drive the instrument arm 5 and the medical instrument 4 held by the arm 5, and the second servo interface 11*b* is provided to drive the scope arm 7 and the scope 6. Each servo interface 11*b* is a digital signal processor (DSP) and processes servo signals at high speed. The first servo driver 11*c* amplifies the output signal of the first DSP 11*b*, so that the signal may be powerful enough to drive the servo motors incorporated in the instrument arm 5. The second servo driver 11*c* amplifies the output signal of the second DSP 11*b*, so that the signal may be powerful enough to drive the servo motors built in the scope arm 7.

As shown in FIG. 2, the controller 11 has a data bus line 11*m*, two analog-signal lines 11*j*, two analog-signal lines 11*k*, and a data line 11*u*. The data bus line 11*m* is used to supply position data from the micro-controller 11*a* to the DSPs 11*b*, encoder feedback data from the arms 5 and 7 to the micro-controller 11*a*, and the data to the micro-controller 11*a* from the up-down counter 11*e*, the magnetic sensor data interface circuit 11*d*, the keyboard interface section 11*f*, the foot switch interface section 11*g* and the floppy disk controller 11*h*. The analog-signal lines 11*j* are provided to supply signals from the DSPs 11*b* to the servo drives 11*c*. The analog-signal lines 11*k* are provided to supply power signals from the servo drives 11*c* to the servo motors incorporated in the arm 5 and 7 and the encoder feedback data from the slave arms 5 and 7 to the micro-controller 11*a* through the servo drivers 11*c*, the analog-signal lines 11*j*, the DSPs 11*b* and the data bus line 11*m*. The data line 11*u* is used to supply data from the floppy disk controller 11*h* to the floppy disk drive 11*i* and vice versa.

The surgical manipulator has two more interfaces 11*t* and 11*s* as shown in FIG. 2. The interface 11*t* connects the foot switch unit 12 and the foot switch interface section 11*g*. The interface 11*s* connects the keyboard 13 and the keyboard interface section 11*f*.

Although not shown in FIG. 2, address buses and control lines are provided in the controller 11, for selecting and controlling the function modules. Further, encoder feedback signal lines (not shown) are provided for supplying the signals from the arms 5 and 7 to the DSP 11*b*, in addition to the analog-signal lines 11*j* and 11*k*.

The controller 11 controls both the scope slave manipulator and the instrument slave manipulator in basically the same method, in accordance with the signals generated by the encoders mounted on the master arm 8 and the data supplied from the HMD 9. It will, therefore, be explained how the controller 11 controls the instrument slave manipulator.

The up-down counter 11*e* reads the data supplied from the encoders on the master arm 8. The counter 11*e* increases or decreases its initial count in accordance with the data, thereby detecting the distance the master arm 8 has been actually moved. The data held in the up-down counter 11*e* is supplied to the micro-controller 11*a* through the data bus line 11*m* at every sampling time. The micro-controller 11*a* performs coordinate transform in accordance with the distance the arm 8 has been moved, thereby to determine how the instrument slave manipulator should be moved.

To control the scope slave manipulator it suffices for the micro-controller 11a to perform reverse coordinate transform, wherein joint variables in link parameters are obtained from the absolute position and inclination of the magnetic sensor 10. (The link parameters are to be supplied to the drive sections of the slave manipulator.) To control the instrument slave manipulator, however, it is necessary for the micro-controller 11a to perform not only reverse coordinate transform but also forward coordinate transform. The forward coordinate transform needs to be carried out before the reverse coordinate transform, in order to determine the position and orientation of the distal portion of the master arm 8. This is because the master arm 8 comprises a plurality of links. How to move the instrument slave manipulator in the same way as the surgeon moves the master arm 8 will be described later in detail.

Once the distance the instrument arm 5 is to be moved has been calculated by means of the coordinate transforms, the data showing this distance is supplied from the micro-controller 11a through the data bus line 11m to the DSP 11b. The DSP 11b processes the input data in accordance with a prescribed algorithm (e.g., simple algorithm such as PID control algorithm), thereby producing control data. The control data, which consists of analog signals, is output via the analog-signal line 11j to the servo driver 11c. The servo driver 11c amplifies the analog signals. The amplified analog signals are supplied through the analog-signal line 11k to the respective motors incorporated in the instrument slave manipulator. In the instrument slave manipulator, the motors drive the mechanisms. As a result, the instrument slave manipulator is moved.

As indicated above, the foot switch unit 12 is operated to set or release the master-slave mode. When the foot switch unit 12 is operated, the controller 11 is temporarily interrupted since the toggle switch 31 is connected to the interrupt terminal INT of the micro-controller 11a as is illustrated in FIG. 3.

The controller 11 is interrupted not only when the foot switch unit 12 is operated, but also when timer interrupt takes places every time the input from the magnetic sensor data interface circuit 11d or the up-down counter 11e is sampled or when alarm interrupt occurs due to a malfunctioning of the servo system, thereby to stop the instrument arm 5. In order to accomplish the alarm interrupt, the controller 11 has an interrupt line (not shown) which connects the DSP 11b to the micro-controller 11a. Several alarm levels are provided such as rotational speed alarm, current alarm, feedback encoder alarm, deviation counter alarm, and the like. It is from any of these alarm level that the micro-controller 11a determines whether the master-slave mode operation should be continued or not. The control program of the micro-controller has been so written as to make the micro-controller 11a stop functioning automatically when the instrument arm 5 makes a fatal error.

The operation of the surgical manipulator system will now be explained.

To use the system to examine the interior of the body cavity of the patient 2 and to perform surgery within the body cavity, the surgeon needs to input commands into the controller 11, thereby to set up the controller 11. When he or she operates the keyboard 13, selecting commands, the HMD 9 he or she wears displays the commands in the form of a setup menu. An example of the setup menu is shown in FIG. 7C. The setup menu may be displayed by a display, such as a CRT display, located near the controller 11. Any person other than the surgeon (for example, a nurse) may operate the keyboard 13 and select command, thereby to set up the controller 11.

Once the controller 11 has been set up, initial control parameters are automatically read from the floppy disk placed in the floppy disk drive 11i. Among the control parameters are: instruction data, master-slave scale ratios, and response of the slave arms 5 and 7. The master-slave scale ratio and the response of the arms 5 and 7 will be described below.

One of the master-slave scale ratios is the ratio of the distance the instrument arm 5 is moved to the distance the master arm 8 is moved. Thus, if the ratio is 1, the arm 5 will be moved by 10 mm when the surgeon moves the master arm 8 by the same distance. If the ratio is 0.1, the arm 5 will be moved by 1 mm when the surgeon moves the master arm 8 by 10 mm. Another master-slave scale ratio is the ratio of the angle through which the arm 5 is rotated to the angle through which the surgeon rotates the master arm 8.

The response of, for example, the scope arm 7 can be changed by adjusting the input sensitivity of the magnetic sensor 10 provided on the HMD 9. If the input sensitivity of the sensor 10 is set at 1 mm, the scope arm 7 will not be moved unless the magnetic sensor 10 moves for 1 mm or more. In this case, the scope arm 7 is prevented from moving even if the surgeon unconsciously moves his or her head but not for a distance longer than 1 mm.

After the controller 11 has been set up and the initial control parameters have been read from the floppy disk, it is necessary to determine the positions the slave arms 5 and 7 assume at present. In other words, the absolute positions of the arms 5 and 7 need to be detected. These positions could be determined from the signals output from the encoders connected to the servo motors incorporated in either slave arm if the encoders were absolute-position encoders. Since absolute-position encoders are very expensive, the encoders connected to the servo motors are incremental encoders, which are far less expensive. Since each incremental encoder used can detect nothing more than a relative amount of motion, both slave arms 5 and 7 must be subjected a return-to-origin operation so that their absolute positions may be determined.

How the return-to-origin operation is carried out will be explained. First, the components of either slave arm are moved until they return to prescribed original positions so that the arm assumes a reference position. Next, the counts the incremental encoders have when the arm components reach the original positions are acquired. Finally, the absolute position of either slave arm is determined from the counts of the encoders. Before effecting the return-to-origin operation, it is necessary to determine in which order the arm components should be returned to their original positions so that they may not collide with any object located near them.

FIG. 7D shows a menu which a control display (not shown) displays under the control of the micro-controller 11a and which instructs the surgeon to set a desired order of returning the arm components to their original positions. The surgeon operates the numeral keys on the keyboard 13, thereby setting a particular order in which the arm components are moved to their original positions. More precisely, the surgeon assigns a number "1" to the arm component which should be the first to return to the original position, a number "2" to the arm component which should be the second to return to the original position, a number "3" to the arm component which should be the third to return to the original position, and so forth. The numbers thus assigned are set by pushing the "set" key (not shown) provided on the keyboard 13. The micro-controller 11a examines the input numbers in accordance with a built-in program, to determine whether or not any number input is identical to any other number input. If there are two or more identical numbers, the micro-controller 11a causes the control display to display a message "IDENTICAL NUMBERS HAVE BEEN SET" in the order-setting menu, instructing the surgeon to make an appropriate order-setting.

The order of returning the arm components to the original positions, which has been set previously in preparation for operating the scope arm 5 and the instrument arm 7, may be saved, in the form of a control parameter, on the floppy disk. In this case, the order is read from the floppy disk along with the other control parameters soon after the controller 11 has been set up, and the arm components are therefore returned to their original positions in the same order as before in preparation for operating the scope arm 5 and the instrument arm 7.

Whether or not to save said order is at the surgeon's discretion. When the surgeon pushes the "operation end" key (not shown) provided on the keyboard 13 at the completion of a surgery, the micro-controller 11a causes the control display to display a question of "DO YOU WANT TO SAVE THE ORDER?" If the surgeon wants to save the order, he or she pushes the "yes" key (not shown) on the keyboard 13, whereby the data representing the order is saved. Otherwise, he or she pushes the "no" key (not shown) on the keyboard 13, whereby the data is destroyed.

When the order in which the arm components have been previously returned to their original positions is read from the floppy disk, the numbers assigned to the respective arm components will be displayed in the menu shown in FIG. 7D. If the surgeon wants the arm components to return to the original positions in the order displayed, he or she pushes the "set" key for each number display. To be more specific, every time the "set" key is pushed while a cursor is displayed below one of the numbers, the cursor moves to the next lower number. If the surgeon wishes to change any number display to another, thereby to alter the order, he or she pushes the numeral key corresponding to the number while the cursor is displayed below that number.

The surgical manipulator system cannot further operate before the completion of the return-to-origin operation. This is solely because incremental encoders are connected the servo motors incorporated in the slave arms 5 and 7. Whether or not the return-to-origin operation has been completed is determined by the micro-controller 11a. The return-to-origin operation need not be performed again as long as the power switch of the controller 11 remains closed, unless it must be effected for a second time for a specific reason. In other words, the return-to-origin operation is performed only once in most cases after the power switch has been closed.

After the return-to-origin operation has been performed, the instrument arm 5 and the scope arm 7 are moved, bringing their distal ends to desired positions above the holes 2a cut in the abdominal body wall of the patient 2 who is laying on the operating table 1. The arms 5 and 7 are so moved by depressing the numeral keys on the keyboard 13. More specifically, the "1" key is pushed to move that component of either slave arm which is closest to the table 1, the "2" key is operated to move that component of the arm which is second closest to the table 1, and so forth. After both slave arms 5 and 7 have been so moved, the "set" key is pushed, whereby the arms 5 and 7 are held at those positions; with their distal ends set above the holes 2a incised in the patient's abdominal wall. Then, the medical instrument 4 and the scope 6 are attached to the distal ends of the slave arms 5 and 7, respectively, taking appropriate positions with respect to the holes 2a.

Now that the instrument 4 and the scope 6 are held by the slave arms 5 and 7 and appropriately positioned with respect to the holes 2a, the surgeon can operate the surgical manipulator system in the master-slave mode, in order to examine the interior of the patient's body cavity and to perform surgery therein. Dialog menus may be display by the HMD 9 to inform the surgeon which step of the surgery he or she has already completed and which step of surgery he or she has yet to carry out. This would make it easier for the surgeon to perform the surgery.

It will now be explained how the surgeon operates the system in the master-slave mode.

As described above, the foot switch 12 has two foot switches 12a and 12b. The surgeon depresses either foot switch two times in a predetermined period, whereby the system is set into the master-slave mode. To release the system from the master-slave mode, it suffices for the surgeon to tread on either foot switch only once. Whichever foot switch, the switch 12a or the switch 12b, is operated, the controller 11 responds to set or release the slave-master mode in accordance with the number of times the switch has been trod on.

Two foot switches 12a and 12b are provided in order to increase and decrease each of the control parameters explained above. When the first foot switch 12a is depressed, a control parameter (e.g., the master-slave scale ratio or the response of either slave arm) is increased. Conversely, when the second foot switch 12b is depressed, the control parameter is deceased.

If the surgeon depresses either foot switch (12a or 12b) twice, thus setting the system into the master-slave mode, the HMD 9 will display a pop-up menu shown in FIG. 7B, in the left-side part of the HMD screen as depicted in FIG. 7A. If the surgeon treads on the first foot switch 12a, the cursor will move downwards in the menu. If he or she treads on the second foot switch 12b, the cursor will move upwards in the menu. If either foot switch is depressed twice quickly, the item at which the cursor is displayed is selected.

Assume that the surgeon wearing the HMD 9 and holding the master arm 8 treads upon either the switch 12a or 12b twice in a predetermined period, thereby setting the system into the master-slave mode. When the surgeon moves the master arm 8 such that the distal end of the arm moves along the Z axis of a 3-dimensional coordinate system, as indicated by the broken line in FIG. 4A, the distal end of the instrument arm 5 is moved along the Z axis, too, as illustrated in FIG. 4B. That is, the vector S of the distal end of the arm 5 is moved in the same way as the vector M of the distal end of the master arm 8. This remote control of the instrument arm 5 is achieved since the micro-controller 11a performs the coordinate transform which has been described above.

By virtue of the coordinate transform, when the surgeon moves the master arm 8, thereby moving the distal end thereof along the Y axis of the 3-dimensional coordinate system as shown in FIG. 4A, the instrument arm 5 is moved along the Y axis, too, the instrument 4 held by the arm 5 is oriented in the Y axis, and the distal portion of the instrument 4 is bent. In this instance, the master-slave scale ratio is set at 0.5, and the instrument arm 5 is moved half the distance the surgeon has moved the master arm 8.

The scope slave manipulator is controlled as the surgeon wearing the HMD 9 moves his or her head to observe an image of an object existing in the body cavity. To state more precisely, as the surgeon moves the head and, hence, the HMD 9, the scope arm 7 and the scope 6 held by the arm 7 are moved. For example, when the surgeon moves his or her head forward, thus moving the HMD 9 from point P to point Q along a broken line as shown in FIG. 5A, the scope 6 is moved from point S to point T along a broken line as illustrated in FIG. 5B.

As indicated above, both slave arms 5 and 7 are remote-controlled as the surgeon wearing the HMD 9 operates the master arm 8 and moves his or her head.

To perform the above-described coordinate transform, the micro-controller 11a defines two reference coordinate systems for the master arm 8 and the instrument slave manipulator, respectively. In the first embodiment, the micro-controller 11a defines a reference coordinate system XYZ of the master arm 8 based on the position and orientation which the distal end of the master arm 8 takes when the system is set into the master-slave mode, and a reference coordinate system XYZ of the instrument slave manipulator based on the position the distal end of the instrument slave manipulator assumes when the system is set into the master-slave mode.

When the surgeon moves the master arm 8, the micro-controller 11a performs coordinate transform, thereby determining the distance and direction in which the xyz coordinate system of the distal end of the master arm 8 has been moved from the reference coordinate system XYZ. Based on the distance and the direction thus determined, the instrument slave manipulator is controlled. To use robotics terminology, this method is to align the mechanical interface of the instrument slave manipulator with that of the master arm 8. The method can define any reference coordinate system for the master arm 8, making it possible to control the instrument slave manipulator by operating the master arm 8, no matter whichever position the master arm 8 takes.

Figure 8B:
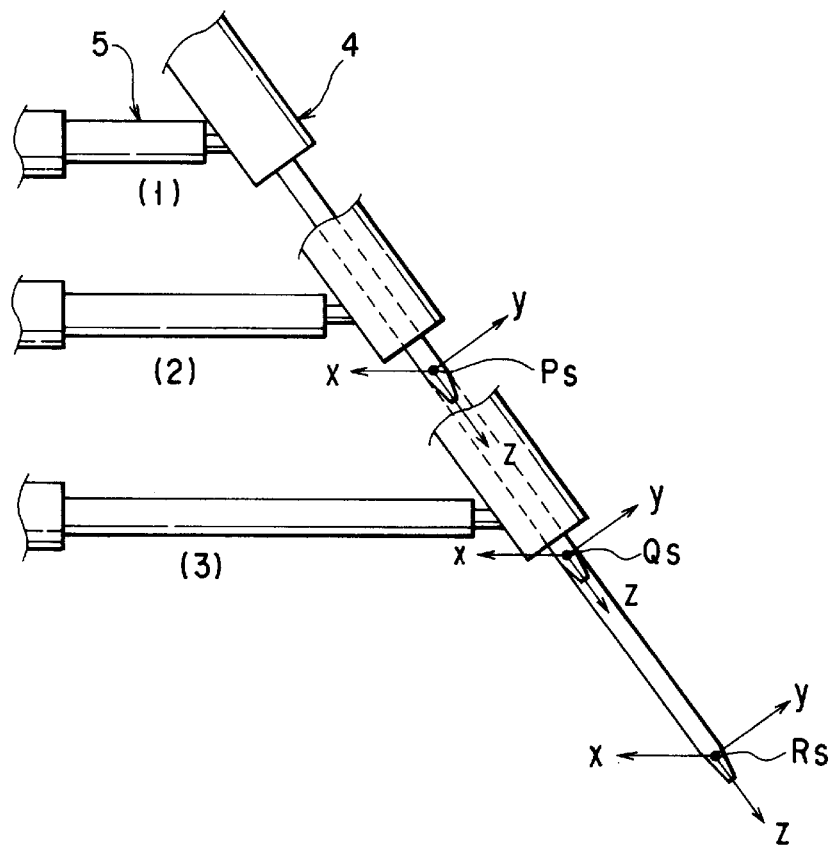
FIG. 8B is a diagram showing how the instrument arm is moved as the surgeon operates the master arm.

The master arm 8 may assume the position depicted by the solid lines shown in FIG. 8A when the surgical manipulator system is set into the master-slave mode, and may take the position indicated by the broken lines shown in FIG. 8A when the xyz coordinate system of the arm 8 is moved along a dot-dash line or in the +Z direction. The instrument slave manipulator may assume the position (1) shown in FIG. 8B when the surgical manipulator system is set into the master-slave mode. Assume the instrument slave manipulator is moved to take the position (2) shown in FIG. 8B, having its distal end moved from point $P_S$ to point $Q_S$, when the surgeon moves the master arm 8, moving its distal end from point $P_M$ to point $Q_M$ as shown in FIG. 8A. The moment the distal end of the master arm 8 reaches point $Q_M$, the master arm 8 can no longer be moved further in the +Z direction because of its mechanical restriction. Therefore, the instrument slave manipulator cannot be moved to have its distal end move to point $R_S$ which is farther from point $Q_S$. In other words, the instrument slave manipulator cannot take the position (3) shown in FIG. 8B.

To move the instrument slave manipulator to the position (3), the surgeon releases the system from the master-slave mode and moves the master arm 8 in the −Z direction, back to the initial position indicated by the solid lines in FIG. 8A. Then, the surgeon sets the system into the master-slave mode again and moves the master arm 8 in the +Z direction. As a result, the instrument slave manipulator is moved such that its distal end moves from the point $Q_S$ to the point $R_S$. Thus, the instrument slave manipulator assumes the position (3) shown in FIG. 8B.

As has been explained, as long as the surgical manipulator system remains in the master-slave mode, the distal end of the instrument slave manipulator can be moved in the same way as the surgeon moves the master arm 8, whatever position the master arm 8 assumes immediately before it is moved. Moreover, even if the master arm 8 can no longer be moved in a specific direction due its mechanical restriction, the instrument slave manipulator can be further moved by releasing the system from the master-slave mode, then moving the master arm 8 in the opposite direction, next setting the system back into the master-slave mode and finally moving the master arm further in the same direction as before.

How to change the control parameters during the surgical operation will be explained in detail.

Assume that the surgeon moves his or her head, thereby seeing the image of a desired object present in the body cavity. Then, the surgeon can start applying treatment to the object, while observing the image of the object. It may be desirable that the master-slave scale ratio be set at a value greater than 1.0, enabling the surgeon to quickly guide the instrument 4 to the object in the body cavity. Once the instrument 4 is properly positioned in the body cavity, it is then desirable that the master-slave scale ratio be set at a value less than 1.0. This is because the object is very small as compared with the body cavity. Unless the scale ratio is set at such a small value, the instrument arm 5 may be moved excessively as the surgeon moves the master arm 8. Should it happen, the distal end of the instrument 4 would be moved too much and abut another object which requires no treatment, inevitably damaging this object.

To allow the surgeon to alter the master-slave scale ratio at any time during the surgical operation, the HMD 9 displays the pop-up menu shown in FIG. 7B when the surgeon depresses either foot switch (12a or 12b) once, thereby releasing the surgical manipulator system from the master-slave mode. It suffices for the surgeon to tread on the foot switch 12a to increase the master-slave scale ratio, and the foot switch 12b to decrease the master-slave scale ratio. More precisely, when the first foot switch 12a is depressed, the icon with an upward arrow blinks and the master-slave scale increases gradually. Similarly, when the second foot switch 12b is depressed, the icon with a downward arrow blinks and the master-slave scale decreases gradually. The longer the surgeon keeps treading on either foot switch, the greater the master-slave scale ratio will be changed. (The unit value by which the scale ratio is changed was set when the controller 11 was set up.) The surgeon can therefore alter the master-slave scale ration whenever he or she wants while performing the surgery on the object.

To set the surgical manipulator system back into the master-slave mode after setting the master-slave scale ratio at a desired value, the surgeon only needs to tread the foot switch 12a or 12b twice in predetermined period.

The master-slave mode program is terminated when a specified key on the keyboard 13, for example the "Q" key, is depressed. No instructions are supplied to either slave manipulator once the surgeon has trod on either foot switch once, thus releasing the system from the master-slave mode. The slave manipulators would not operate at all thereafter even if the surgeon wearing the HMD 9 walks toward the controller 11 in order to operate the keyboard 13. When the surgeon pushes the "Q" key on the keyboard 13, the master-slave mode program is terminated. After the program has been terminated, the surgeon can alter the control parameters (thereby to, for example, switching the item set by the switch unit 12, from the master-slave scale ratio to the slave-arm response), and can set the surgical manipulator system into the master-slave mode again.

With the surgical manipulator system according to the first embodiment it is possible to change the control parameters such as the scale ratio between the master arm 8 and the instrument 4 and the scale ratio between the HMD 9 and the scope 6. The operability of the system is therefore high. In other words, the slave manipulators can be moved at such a ratio to the motion of the master arm and the HMD, that the surgeon may remote-control the instrument 4 and the scope 6 appropriately.

In the first embodiment described above, it is impossible to alter the master-slave scale ratios for the instrument manipulator and the scope manipulator, independently of each other.

The second embodiment of the invention will be described, in which the instrument manipulator and the scope manipulator can be operated at different master-slave scale ratios.

In the second embodiment, a hierarchy menu is used to operate the instrument manipulator and the scope manipulator at different master-slave scale ratios. For example, the HMD 9 displays an upper-level menu when the surgeon treads on a foot switch 12 three times in a predetermined period, and displays a lower-level menu when the surgeon treads on the foot switch 12 two times in a predetermined period. When the surgeon treads on the foot switch 12 only once, the cursor is selected for the menu the HMD 9 is displaying. Thus, the scale ratios for the instrument manipulator and the scope manipulator can be changed independently, by operating the foot switch 12.

More specifically, the surgeon operates the master switch unit 12 in the following way.

First, the surgeon treads on the foot switch 12a or 12b three times in a predetermined period, setting the system into the master-slave mode. The surgeon can then examine the interior of the patient's body cavity and perform surgery therein, by moving his or her head and operating the master arm 8. As soon as the system is set into the master-slave mode, the HMD 9 displays the scale-ratio selecting menu of FIG. 7E in the part A shown in FIG. 7A.

If the surgeon treads on the foot switch 12a or 12b once in order to change the master-slave scale ratio, the HMD 9 will display a pop-up, which overlaps the scale-ratio changing menu, as is illustrated in FIG. 7F. Seeing this menu, the surgeon treads on the foot switch 12a repeatedly until the scale ratio increases to a desired value, or the foot switch 12b repeatedly until the scale ratio decreases to a desired value. After the master-slave scale ratio has been changed to the desired value, the surgeon treads on either the switch 12a or the switch 12b twice in a predetermined period. The pop-up menu (FIG. 7B) is thereby closed, and only the scale-ratio selecting menu of FIG. 7E remains displayed on the HMD screen. Thus, scale-ratio changing menu can be opened and closed whenever the surgeon wants to change the master-slave scale ratio while carrying out the surgery.

Once the master-slave scale ratio has been changed, the HMD 9 displays the setup menu (FIG. 7C) again, which had been displayed upon closing the power switch to the surgical manipulator system. Thereafter, the master-slave mode can be switched to any other operating mode such as the instruction mode or the playback mode, or the control parameters can be changed.

Since the scale ratios for the instrument manipulator and the scope manipulator can be changed to any desired values and independently of each other, the surgical manipulator system according to the second embodiment is more easy to operate than the system according to the first embodiment.

Another surgical manipulator system which is the third embodiment of the invention will now be described. The third embodiment is characterized in that the responses of both slave manipulators can be altered when the surgery is being performed by using the system, so that another surgeon may take up the surgery from the surgeon.

With the first and second embodiments it is possible for the surgeon to change the master-slave scale ratio to any desired value after he or she has set the system into the master-slave mode. The third embodiment is designed to enable a surgeon to change the responses of both slave manipulators so that he or she can easily perform the surgery which he or she has taken over from the surgeon who has been carrying the surgery.

As is known, the distance and speed the master arms and the HMD are moved entirely depend upon the surgeon's habit. Hence, a surgeon finds it difficult to operate the master arm 8 properly to perform surgery successfully if the responses of both slave manipulators remain at the values his or her colleagues has set. In the case where the surgeon takes over the surgery from the colleagues, he or she needs to alter the responses of the slave manipulators to the values suitable for him or her.

How to alter the response of, for example, the response of the scope slave manipulator will be explained. The surgeon may unconsciously move his or her head while performing the surgery and wearing the HMD 9. Assume that the head moves up and down as shown in FIG. 6A. The magnetic sensor 10 detects the position change of the HMD 9 (or the position change of the surgeon's head). Based on the position change detected by the sensor 10 the controller 11 controls the scope slave manipulator.

Were its response set at an excessively large value, the scope slave manipulator should vibrate as the surgeon may unconsciously move his or her head up and down as illustrated in FIG. 6A. If so vibrated, the manipulator may cause pain on the part of the patient. The scope slave manipulator may cause the same inconvenience if the surgeon may unconsciously move the head sideways as shown in FIG. 6B.

In order to prevent such inconvenience, a threshold value is imparted to the response of the scope slave manipulator so that the manipulator is not driven at all unless the signal output by the magnetic sensor 10 has a magnitude which is greater than the threshold value. To be more specific, a filter program is inserted into the program built in the micro-controller 11a. The filter program prevents the scope slave manipulator from operating unless the output signal of the magnetic sensor 10 represents that the HMD 9 has moved for a distance longer than 1 mm.

The micro-controller 11a executes the filter program, thereby finding the distance in magnitude between the last two output signals the sensor 10 has generated. From this difference the distance the HMD 9 has moved is determined. The distance, thus determined, is compared with the response, i.e., 1 mm, set for the sensor slave manipulator. If the distance is greater than the response preset for the sensor slave manipulator, the output signal of the magnetic sensor 10 is supplied to the DSP 11b and used as data which represents the position of the HMD 9. The DSP 11b processes the input data, producing an analog control signal.

The control signal is supplied via the analog-signal line 11*j* to the servo driver 11*c*, which amplifies the analog control signal. The amplified signal is supplied through the analog-signal line 11*k* to the respective motors incorporated in the scope slave manipulator. As a result, the scope slave manipulator is controlled. If the distance is equal to or less than the response preset for the sensor slave manipulator, the output signal of the magnetic sensor 10 is not supplied to the DSP 11*b*. Thus, the response of the scope slave manipulator can be easily adjusted by using the filter program which is added as a subroutine to the program built in the micro-controller 11*a*.

More specifically, the surgeon who has taken over changes the response of the scope slave manipulator to a desired value, in the following way. First, he or she treads on either foot switch 12*a* or 12*b*, releasing the system from the master-slave mode. Next he or she operates the foot switch unit 12, thereby causing the HMD 9 to display a response changing menu in the part A shown in FIG. 7A. Then, seeing this menu, the surgeon operates the foot switch 12, thus increasing or decreasing the response to the desired value and setting the system into the master-slave mode again—in the same way as he or she may change the master-slave scale ratio. The response changing menu is identical to the scale-ratio selecting menu of FIG. 7E, except that the word "RESPONSE" is displayed in place of the word "SCALE." Needless to say, the surgeon can alter the response of the instrument slave manipulator in exactly the same manner as he or she changes the response of the scope slave manipulator.

As explained above, with the third embodiment the surgeon who has just taken over the surgical operation from the colleague can change the response of either slave manipulator to the very value him or her wants.

Another surgical manipulator system which is the fourth embodiment of the invention will be described. The fourth embodiment is characterized in both slave manipulators are not moved further when the surgeon moves the master slave 8 and the HMD 9 for a distance longer than a preset value. In the first embodiment, the instrument 4 and the scope 6 may inflict injury on the patient 2 when the surgeon moves the master arm 5 and the HMD 9 too fast, since the motion of the arm 8 and that of the HMD 9 are transmitted faithfully to the instrument 4 and the scope 6, respectively.

In the fourth embodiment, the motion of the master arm 8 and the motion of the HMD 9 are not transmitted to the instrument 4 and the scope 6, respectively, when the surgeon moves the arm 8 and the HMD 9 too fast, either consciously or unconsciously. To be more specific, the micro-controller 11*a* is programmed to generate an alarm signal and a stop signal when the input data represents that the arm 8 and the HMD 9 are moved faster than a predetermined speed. The alarm signal is supplied to an alarm device 11*w* (FIG. 2). The alarm device 11*w* generates an alarm, informing the surgeon that he or she has moved the master arm 8 or the HMD 9 too fast. The stop signal is supplied via the DSPs 11*b* to the servo drivers 11*c*. In response to the stop signal, the servo drivers 11*c* stop the instrument arm 5 and the scope arm 7 temporarily, respectively. If the surgeon moves the master arm 8 or his or her head much faster than the predetermined speed, the control program of the micro-controller may be automatically terminated. Hence, when the surgeon moves the master arm 8 and the HMD 9 too fast, the instrument 4 and the scope 6 are automatically stopped and will not inflict injury on the patient 2.

The data representing the initial position of the HMD 9 is stored in the magnetic sensor data interface circuit 11*d*, and the data representing the initial position of the master arm 8 is stored in the up-down counter 11*e*. Therefore, both slave manipulators can be automatically moved at a prescribed speed to the positions corresponding to the initial positions of the master arm 8 and the HMD 9 after they are stopped due to the excessively fast motions of the master arm 8 and the HMD 9. As a result, the positional relation between the master arm 8 and the instrument slave manipulator can, and so can be restored the positional relation between the scope slave manipulator and the HMD 9 be restored.

When the surgeon hears the alarm generated by the alarm device 11*w*, he or she knows that he or she has moved the master arm 8 or his or her head at an excessively high speed. The surgeon can then be more careful in operating the master arm 8 and moving his or her head thereafter. The alarm device 11*w* may be placed by a light-emitting device or a vibrator. If this is the case, the surgeon understands that he or she has moved the arm 8 or the head too fast, when he or she perceive the light emitted by the light-emitting device or the vibration generated by the vibrator.

As described above, the motion of the master arm 8 and the motion of the HMD 9 are not transmitted to the instrument 4 and the scope 6, respectively, when the surgeon moves the arm 8 and the HMD 9 too fast, either consciously or unconsciously. In view of this, the surgical manipulator system according to the fourth enables the surgeon to carry out the surgery in safety.

Still another surgical manipulator system, which is the fifth embodiment of the invention, will be now explained.

In the first and second embodiments, the master-slave scale ratios are changed to enhance the operability of the system. That is, the surgeon alters the ratio between the distances the master arm 8 and the instrument 4 are moved and also the ratio between the distances the magnetic sensor 10 and the scope 6 are moved are changed, so that he or she may operate the system with ease. The master-slave scale ratios need not be changed by operating the foot switch unit 12 repeatedly, however, if the same surgeon operates the system to perform the same surgical operation.

The surgical manipulator system according to the fifth embodiment is suitable for this case. It enables a surgeon to move the master arm 8 and the HMD 9 coarsely first, and then to move them minutely, to position the instrument 4 and the scope 6 to appropriate positions with respect to the object which he or she will treat. More precisely, the controller 11 is set into coarse control mode when the surgeon treads on either foot switch (12*a* or 12*b*) once, and into minute control mode when the surgeon treads on either foot switch (12*a* or 12*b*) twice. The master-slave scale ratio for the coarse control and the master-slave scale ratio for the minute control may either be stored in the memory which is incorporated in the micro-controller 11*a*, or be input by operating the keyboard 13. Obviously, the fifth embodiment is easy to operate.

A surgical manipulator system according to the sixth embodiment of the invention will be described, with reference to FIGS. 9, 10, 11A, 11B, 12A, 12B, 13 and 14. The sixth embodiment is characterized in that the slave manipulator assumes the position and orientation which correspond to those of the master manipulator so that the instrument held by the slave manipulator may apply no excessive force at the hole which is cut in the body wall of the patient and through which the instrument is inserted into the body cavity.

Figure 9:
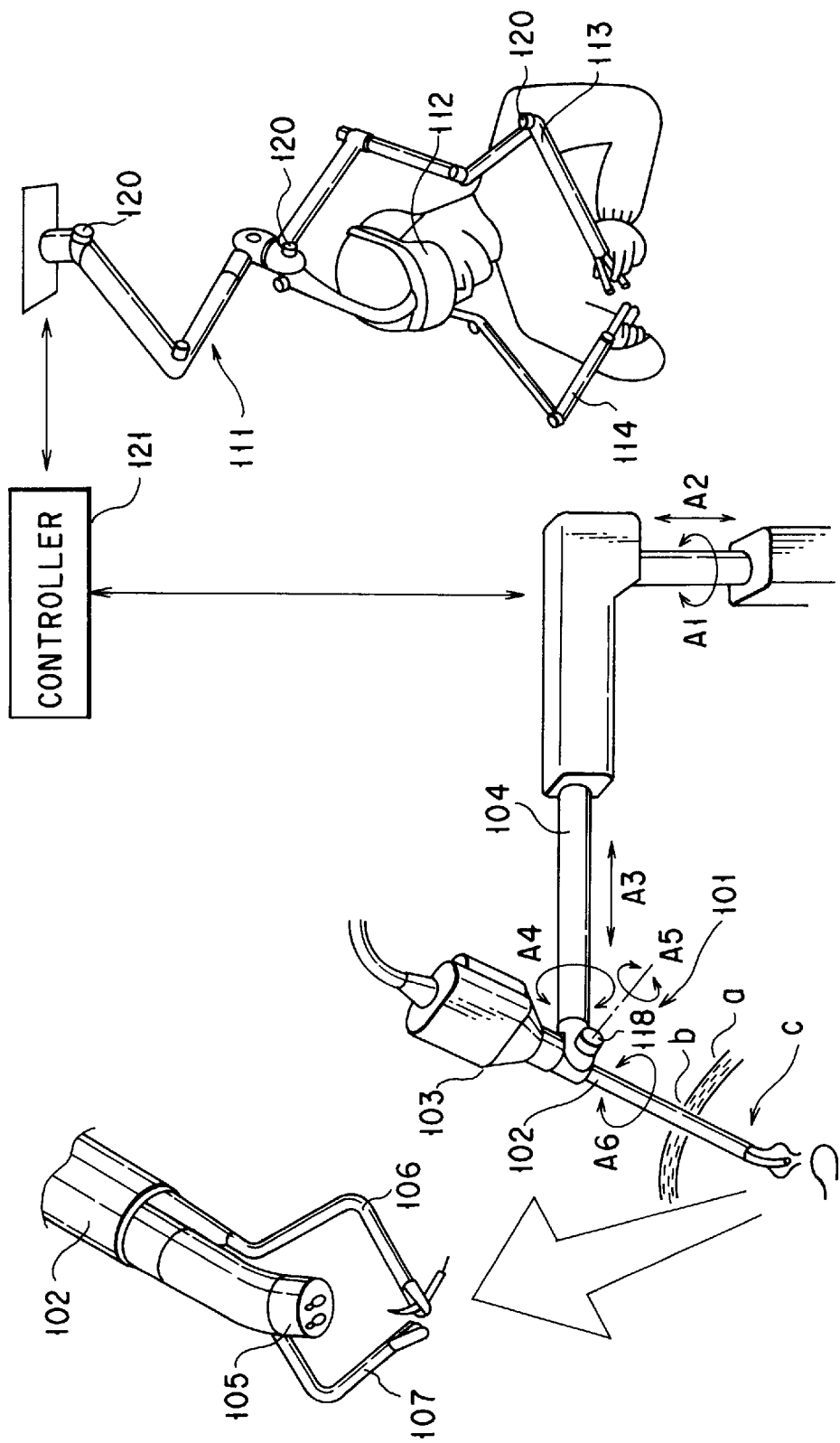
FIG. 9 shows a surgical manipulator system which is a sixth embodiment of the present invention.

As shown in FIG. 9, the surgical manipulator system comprises a slave manipulator 101 and a master manipulator 111. The slave manipulator 101 comprises a medical device 103 and a robot 104 for holding the device 103. The medical instrument 103 has an insertion section 102 which can be inserted into a body cavity c of a patient through a hole b cut in the body wall a of the patient. The robot 104 comprises a plurality of arms. Hence, it has many degrees of freedom, capable of moving linearly and rotating the medical device 103. Attached to the distal end of the insertion section 102 of the device 103 are a three-dimensional scope 105 and a pair of medical instruments 106 an 107. The distal portion of the scope 105 can be bent in various directions. The distal portions of the instruments 106 and 107 can be bent in various directions, too.

The master manipulator 111 has a multi-joint structure. A HMD 112 is coupled to the distal end of the master manipulator 111 by an arm. Also coupled to the distal end of the master manipulator 111 are a pair of master arms 113 and 114 which a surgeon operates to remote-control the medical instruments 106 and 107.

Both the slave manipulator 101 and the master manipulator 111 are connected to a controller 121. The controller 121 controls the slave manipulator 101 so that the distal portion of the slave manipulator 101 may be oriented in the same way as the distal portion of the master manipulator 111, the distal portion of the scope 105 may be bent in the same direction and by the same angle as the arm connecting the HMD 112 to the master manipulator 111, and the medical instruments 106 and 107 may be moved in the same way as the master arms 113 and 114.

The robot 104 has actuators (not shown) such as electric motors, encoders 118, and reduction mechanisms (not shown). One actuator, one encoder, and one reduction mechanism are provided for each of the arms the robot 104 has. Furthermore, encoders 120 are provided at the joints of the master manipulator 111, at one end of the arm connecting the HMD 112 to the master manipulator 111, and at the joints of the master arms 113 and 114.

As shown in FIG. 9, the insertion section 102 incorporates the three-dimensional scope 105 and the medical instruments 106 and 107. Instead, the section 102 may incorporate the scope 105 only, or the instruments 106 and 107 only. The scope 105 is a flexible one, having a bending mechanism in its distal end. Nonetheless, it may be replaced by a rigid scope.

Figure 11A:
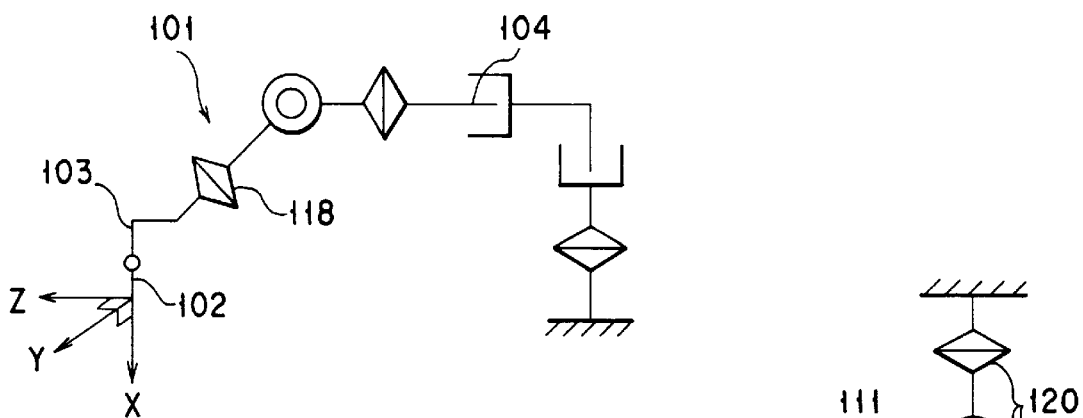
FIG. 11A is a schematic representation of the slave manipulator used in the system shown in FIG. 9.
Figure 11B:
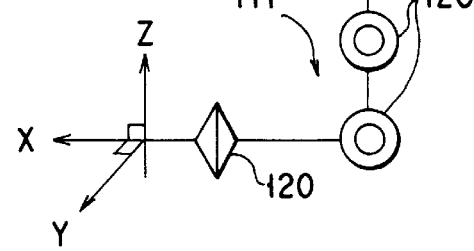
FIG. 11B is a schematic representation of the master manipulator used in the system shown in FIG. 9.

FIG. 11A schematically illustrates the link mechanism of the slave manipulator 101, and FIG. 11B schematically depicts the link mechanism of the master manipulator 111.

Figure 10:
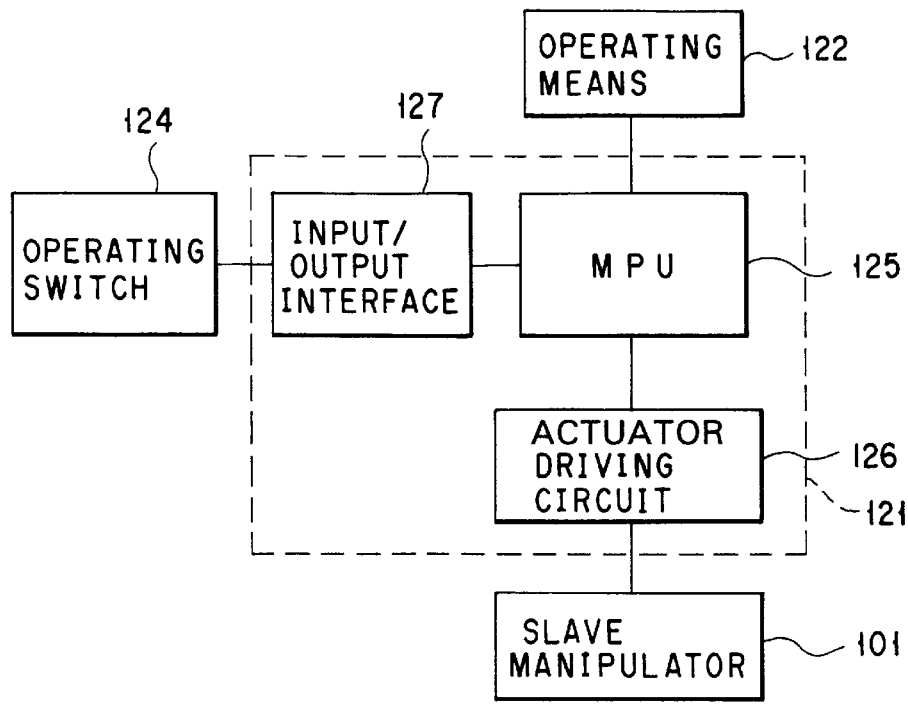
FIG. 10 is a block diagram of the control section incorporated in the surgical manipulator system shown in FIG. 9.

FIG. 10 is a block diagram of the control section of the surgical manipulator system shown in FIG. 9. As shown in FIG. 10, the control section comprises the controller 121, an operating means 122, and an operation switch 124. The controller 121 has an MPU 125, an actuator driving circuit 126, and an input/output interface 127. The MPU 125 is connected to the operation means 122, the actuator driving circuit 126 to the slave manipulator 101, and the input/output interface 127 to the operation switch 124. The controller 121 performs the same function as the controller 11 shown in FIG. 2.

The operation of the surgical manipulator system which is the sixth embodiment of the invention will now be explained.

First, the slave manipulator 101 is point-locked. In other words, the slave manipulator 101 is set into a "point-locked" state (first control mode) to allow the medical instrument 103, which is partly inserted into the body cavity c, to rotate only around the hole b, as if the hole b were a fulcrum.

Hence, once the slave manipulator 101 has been point-locked, the device 103 will not apply an excessive force to the body wall a even if the surgeon moves the master manipulator 111 by mistake. How to point-lock the slave manipulator 101 will be explained in detail, with reference to FIGS. 12A and 12B.

Figure 12A:
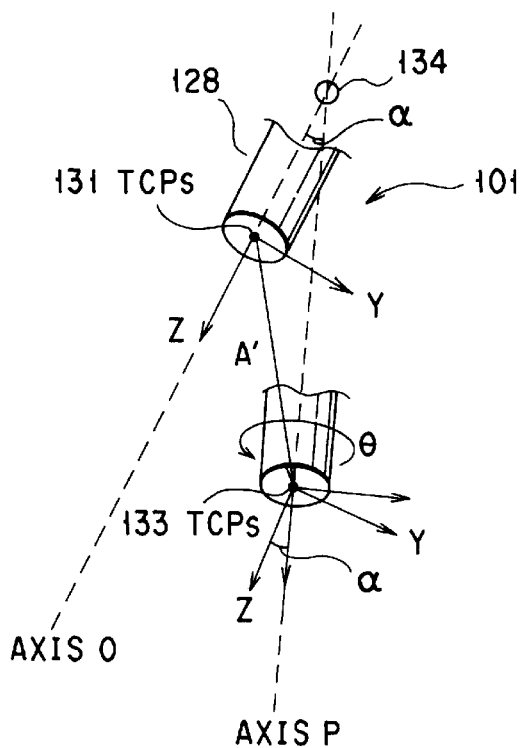
FIGS. 12A and 12B are diagrams explaining how the system of FIG. 9 operates.
Figure 12B:
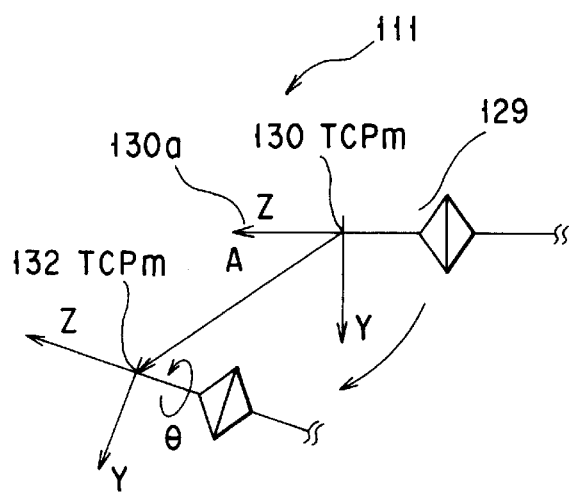

FIG. 12A shows the distal portion 128 of the insertion section 102 of the manipulator 101, and FIG. 12B the distal portion 129 of the master manipulator 111. In the master-slave mode, the distal portion 128 of the slave manipulator 101 is moved in the same way as the surgeon moves the distal portion 129 of the master manipulator 111. Assume that the distal portion 129 of the master manipulator 111 is located at a TCPm 130 as illustrated in FIG. 12B, and that the distal portion 128 of the slave manipulator 101 is located at a TCPs 131. (TCP stands for "Top Center Point.") The process of obtaining the TCP of the master manipulator 111 and slave manipulator 101, thereby to move the slave manipulator 101 consists of forward coordinate transform and reverse coordinate transform. The forward coordinate transform is effected to obtain joint variables from the signals output from the encoders provided at the joints of the master manipulator 111, thereby to determine the position of the TCP and the orientation of the master manipulator 111. The reverse coordinate transform is carried out to obtain based on the TCP of the master manipulator 111 the angles by which the respective arms of the slave manipulator 101 must be rotated.

Assume that the surgeon operates the master manipulator 111, moving the distal portion 129 from TCPm 130 to TCPm 132 as illustrated in FIG. 12B. This motion of the distal portion 129 is indicated by a vector A. Further assume that the surgeon rotates the distal portion 129 in the direction of arrow θ. In this case, the controller 121 obtains a coordinate transform matrix A' (or the vector connecting the TCPs 131 and TCPs 133 shown in FIG. 12A) which is identical to the coordinate transform matrix A (shown also in FIG. 12B) representing the position of the master manipulator 111. Further, the controller 121 obtains an angle α defined by axes O and P and a vector Q perpendicular to the plane defined by the axes O and P, where the axis O connects TCPs 131 and the point-lock position 134 of the slave manipulator 101 and the axis P connects the position 134 and TCPs 133.

To move the distal portion 128 of the slave manipulator 101 in the same way as the surgeon moves the distal portion 129 of the master manipulator 111, the TCPs 131 of the distal portion of the manipulator 101 is moved to the TCPs 133. In this process, the distal portion 128 of the manipulator 101 is moved toward TCPs 133 and rotated around the vector Q by the angle α, whereby the axis of the distal portion 128 passes the point-lock position 134 of the manipulator 101. At the same time, the distal portion 128 is rotated around the axis P by the angle θ as the surgeon rotates the distal portion 129 of the master manipulator 111 by the same angle θ as shown in FIG. 12B.

The controller 121 repeatedly controls the slave manipulator 101 as described above, at predetermined intervals. As a result, the surgical manipulator system is operated in real time in point-locked master-slave mode.

The above explanation holds true of the case where the slave manipulator 101 is inserted in part into the body cavity c of the patient. As the slave manipulator 101 is inserted into the body cavity c or pulled therefrom, there will be a singular point. The singular point is a point where the orientation of the robot 104 cannot be determined, though the position thereof can be determined, when the TCP of the manipulator 101 coincides with the position of the hole b. This is because the distal portion 128 of the manipulator 101 can take countless orientations as it is inserted into the body cavity c. The orientation of the robot 104 may not be determined even if the TCP of the manipulator 101 does not coincides with the position of the hole b, since the controller 121 cannot calculate the angle α accurately as long as the distal portion 128 is located near the hole b. How to deal with this singular point will be described below.

In order to solve the problem relating to the singular point, the TCP of the distal portion 128 of the slave manipulator 101 is held at a position where this TCP coincides with the hole b. To hold the TCP at this specific position, the orientation the distal portion 128 should assume when placed at the hole b must be predetermined. This orientation is one of those which the portion 128 take while being inserted into the body cavity c through the hole b. A non-response region is therefore provided near the hole b, allowing the robot 104 to move smoothly even if there exists a singular point.

The operation of the surgical manipulator system according to the sixth embodiment will be explained.

Figure 13:
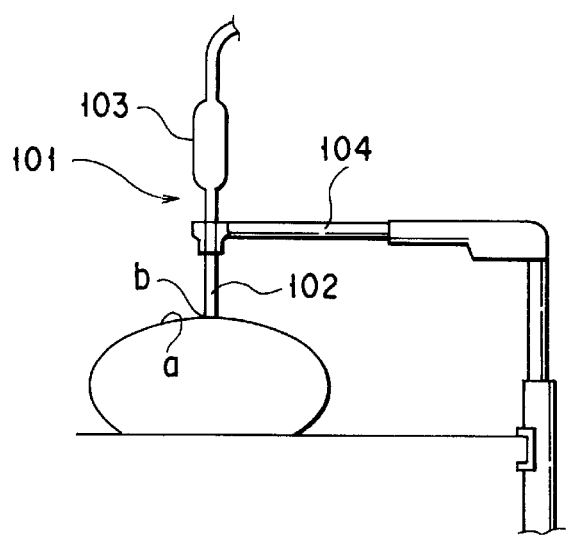
FIG. 13 is a side view of the slave manipulator incorporated in the system of FIG. 9.

First, to determine the position of the hole b, the slave manipulator 101, for example, is oriented as shown in FIG. 13 and the TCP of the manipulator 101 is located at the hole b. (It does not matter how the manipulator 101 is oriented). The TCP of the manipulator 101 may be located after the system has been set into the master-slave mode. Alternatively, it may be located by operation switch 124 (FIG. 10), thereby moving the arms of the slave manipulator 101 independently of one another. Once the TCP of the manipulator 101 has been so located, the positional relation between the manipulator 101 and the hole b is known. The position of the hole b is determined from this positional relation.

Next, the surgeon operates the master manipulator 111. The controller 121 receives the signals from the encoders provided at the joints of the manipulator 111, which are data representing the position and orientation of the master manipulator 111. The controller 121 processes the input data, performing coordinate transform and determining the position and orientation of the master manipulator 111, as can be understood from the flow chart of FIG. 14. Further, the controller 121 determines whether or not the TCP of the distal portion of the slave manipulator 101 is located near the hole b, more precisely in the body cavity c. (It should be noted that the medical device 103 is held at the TCP of the distal portion of the manipulator 101.)

If the TCP of the distal portion of the slave manipulator 101 is located outside the body cavity c, the insertion section 102 of the manipulator 101 is inserted into the hole b, with its inclination not changed at all, and is rotated around its axis by the angle represented by a rotation command supplied to the slave manipulator 101. This is a second control mode.

If the TCP of the distal portion of the slave manipulator 101 is located inside the body cavity c, the insertion section 102 is held, extending through the hole b, that is to say, the insertion section 102 of the slave manipulator 101 has its axis passing through the point-lock position 134, and the TCP of the distal portion of the slave manipulator 101 is located at the position designated by moving the master manipulator 111.

With the sixth embodiment it is possible to move the slave manipulator 101 to enable the distal portion 128 to have its axis passing through the point-lock position 134, even if the manipulator 101 fails to be positioned or oriented so as to hold the medical instrument 103 at an appropriate position with respect to the hole b, when the surgeon operates the master manipulator 111. As a result, the medical device 103 does apply an excessive force to the body wall a.

Since the slave manipulator 101 is moved in the same way as the master manipulator 111 is moved by the surgeon, the distal portion of the device 103 can be moved to any desired position within the body cavity c.

Moreover, the surgeon wearing the HMD 112 can see the image of the interior of the body cavity c while carrying out the surgery, as if he or she were in the body cavity c. This is because, the three-dimensional scope 105 provided in the distal portion of the manipulator 101 is moved in the body cavity c as the controller 121 controls the distal portion the manipulator 101 in accordance with the encoders 120 which are provided at the joints of the master manipulator 111 to which HMD 112 is coupled.

A surgical manipulator system according to the seventh embodiment of the invention will be described, with reference to FIGS. 15, 16A, 16B and 17. The seventh embodiment is characterized by the use of force sensors which are mounted on slave manipulator. The force sensors serve to determine a position and an orientation the slave manipulator may assume so that the medical instrument held by the slave manipulator may not apply an excessive force at the hole which is cut in a body wall and through which the instrument is partly inserted into the body cavity.

Figure 15:
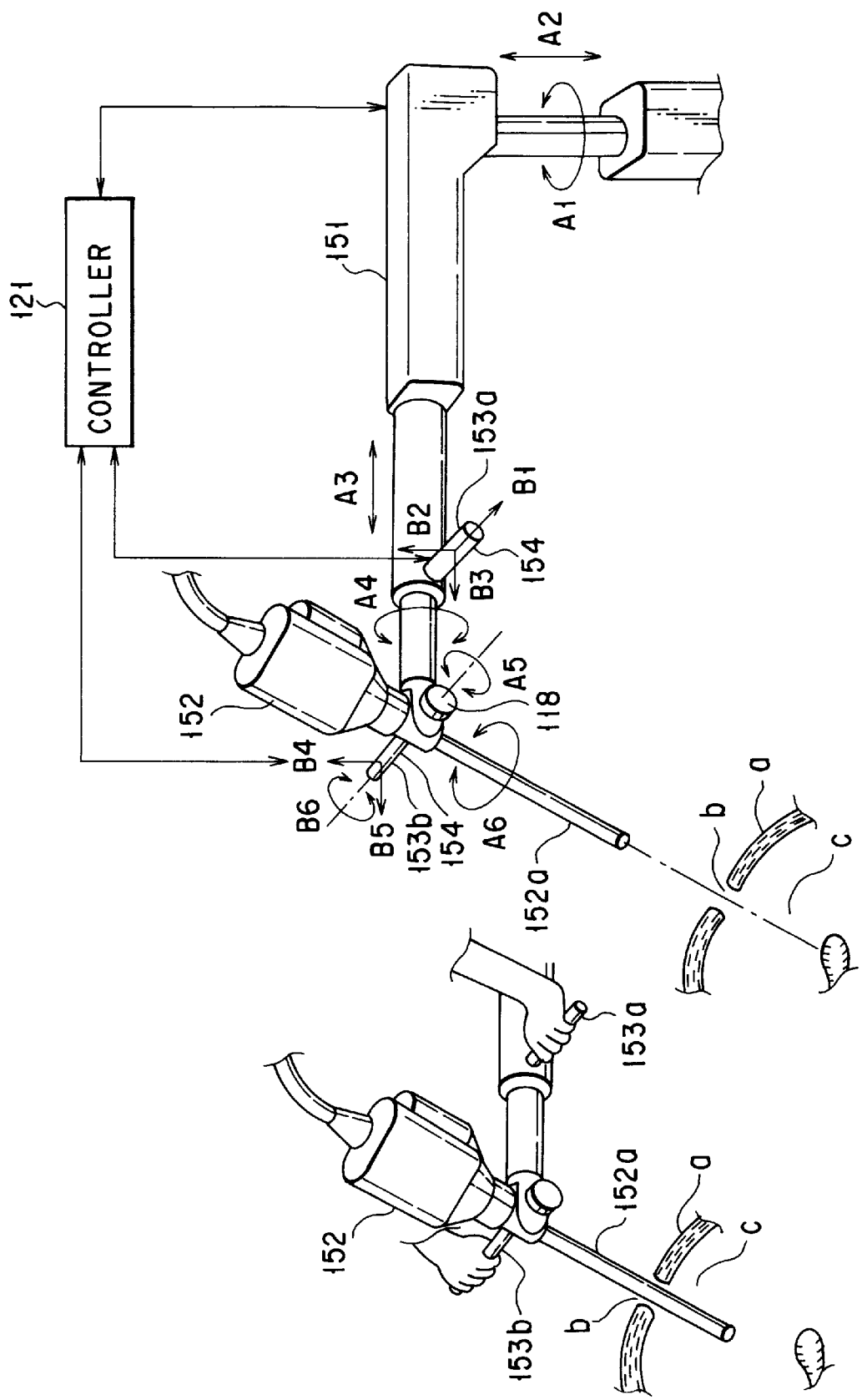
FIG. 15 is a diagram illustrating a surgical manipulator system which is a seventh embodiment of the present invention.

As shown in FIG. 15, the slave manipulator 151 of the system holds an endoscope 152 which has an insertion section 152a. The distal portion of the insertion section 152a can be inserted into a body cavity c through a hole b cut in the body wall a of a patient. The slave manipulator 151 has two handles 154. Two force sensors 153a and 153b are mounted on the handles 154, respectively. The slave manipulator 151 and both force sensors 153a and 153b are connected to a controller 121. The controller 121 controls the slave manipulator 151 so that the manipulator 151 may take the position and orientation which are determined from the signals generated by the force sensors 153a and 153b.

The slave manipulator 151 comprises a plurality of arms and has actuators (not shown) such as electric motors, encoders 118, and reduction mechanisms (not shown). One actuator, one encoder, and one reduction mechanism are provided for each of the arms of the slave manipulator 151. The force sensor 153a contains a strain gauge for detecting three vectors B1, B2 and B3 indicating the directions in which the surgeon applies forces to the sensor 153a. The force sensor 153b contains a strain gauge which can detect two vectors B4 and B5 indicating the directions in which the surgeon applies to the sensor 153b and also an angle B6 through which the surgeon rotates the handle 154.

The endoscope 152 may be replaced by a medical instrument which comprises an endoscope and an insertion section or by a medical instrument which comprises neither an endoscope nor an insertion section. The endoscope 152 may have a bending mechanism in its distal portion. The controller 121 is incorporated in the control section of the seventh embodiment, which is identical to the control section shown in FIG. 10 and which will not be described.

The operation of the surgical manipulator system according to the seventh embodiment will be explained.

The force sensors 153a and 153b determine the position and orientation of the slave manipulator 151. In other words, the position and orientation of the manipulator 151 are defined by the vectors B1, B2 and B3 detected by the force sensor 153a and the vectors B4 and B5 and the angle B6 detected by the force sensor 153b. Unless it is point-locked, the slave manipulator 151 is controlled to move in directions A1, A2, A3, A4, A5 and A6 in accordance with the vectors B1, B2, B3, B4 and B5 and the rotation angle B6 which have been detected by the force sensors 153a and 153b. For example, when the force sensor 153a is pushed forward, or in the direction of vector B3, it generates a signal, which causes the arm A3 to extend. Each force sensor may be so operated to generate two or more signals. If this is the case, two or more arms of the slave manipulator 151 will be moved. The controller 121 repeatedly controls the slave manipulator 151 in this manner, at regular intervals. As a result, the surgical manipulator system is operated in so-called "direct move mode," while the slave manipulator 151 remains not point-locked.

Figure 16A:
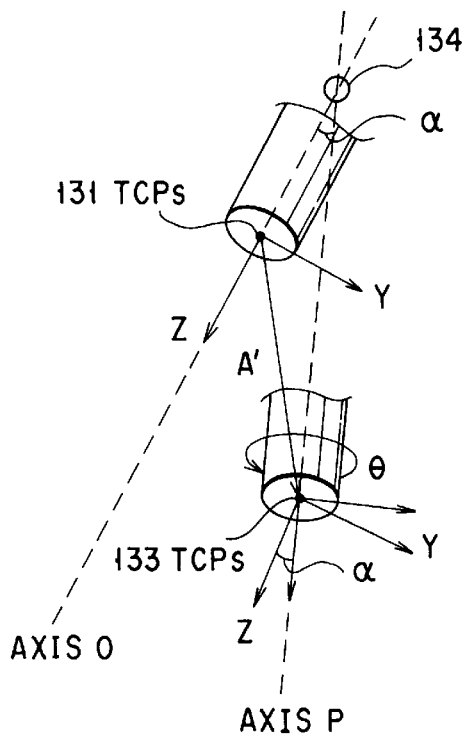
FIGS. 16A and 16B are diagrams for explaining the operation of the system shown in FIG. 15.
Figure 16B:
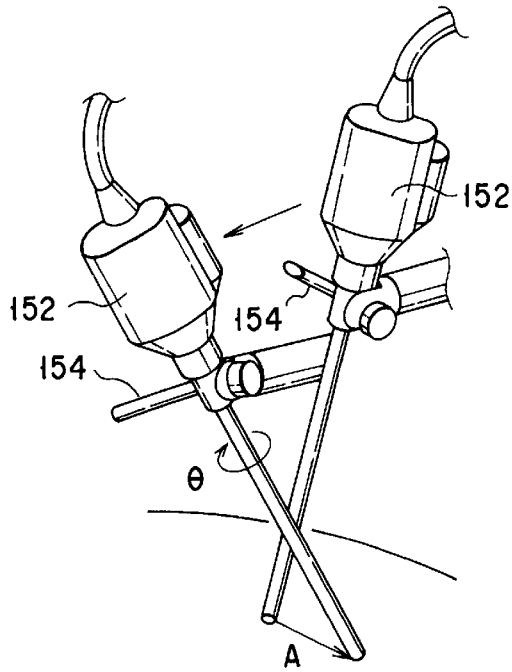

Once the slave manipulator 151 is point-locked, the position which the distal portion of its insertion section 152a takes and the angle at which its insertion section 152a is inclined when the section 152a passes trough the hole b are determined from the position of the distal end of the insertion section 152a which is defined by the vectors B1 to B5. The position and orientation of the insertion section 152a are controlled in accordance with the angle by which the insertion section 152a has been rotated, i.e., the angle B6. More precisely, the surgeon may try to move the endoscope 152 in the direction of the arrow, while holding the handle 154, as shown in FIG. 16B, thereby to move the TCP of the endoscope 152 in the direction of vector A as in the sixth embodiment. Since the force sensors 153a and 153b generate signals representing the vectors B1 to B5 and the angle B6, however, the controller 121 does not perform forward coordinate transform based on the data supplied from the encoders 120 provided at the joints of the master manipulator 111 in order to calculate the vector A showing the direction in which the master manipulator 111 has been moved. That is, the controller 121 calculates neither the position nor orientation of the master manipulator 111. Rather, it uses the data supplied from the force sensors 153a and 153b, i.e., the data representing the motions of the joints of the master manipulator 111, thereby accomplishing the remote control of the slave manipulator 151.

The controller 121 calculates the motion vector A' (FIG. 16A) which extends from the present position of the TCP of the slave manipulator 151 toward the position determined from the signals generated by the force sensors 153a and 153b. Then, the controller 121 defines an axis P, an axis O, an angle α between the axes P and O, and a vector E perpendicular to the plane defined by the axes P and O. It should be noted that the axis P is the line passing the point-lock position 134 and the TCPs 133 (i.e., the end of the motion vector A'), and the axis O is the line which passes the TCPs 131 of the endoscope 152 and which is identical to the axis thereof. The controller 121 effects point-locked control on the slave manipulator, thereby moving the endoscope 152 from the TCPs 131 toward the TCPs 133, rotating the endoscope 152 around the vector E by the angle α. The controller 121 repeatedly controls the slave manipulator 151 in point-locked mode in this way, at regular intervals, whereby the surgical manipulator system is operated in the direct move mode, while the slave manipulator 151 remains point-locked.

As in the sixth embodiment, a non-response region is therefore provided near the hole b, allowing the slave manipulator 151 (and hence the endoscope 152) to move smoothly as the manipulator 151 is inserted into or pulled from the body cavity through the hole b.

FIG. 17 is a flow chart for explaining how the surgical manipulator system of FIG. 15 is operated. The surgeon moves the slave manipulator 151 to a desired position, while holding the handles 154 of the slave manipulator 151. The force sensors 153a and 153b mounted on the handles 154 generate signals, which are supplied to the controller 121. The controller 121 determines whether or not the TCP of the endoscope 152 held by the slave manipulator 151 is located near the hole b, or more precisely, in the body cavity c.

If the TCP of the endoscope 152 is located outside the body cavity c, the insertion section 152a of the endoscope 152 is inserted into the hole b, with its inclination not changed at all, and is rotated around its axis by the angle represented by the signals supplied to the force sensors 153a and 153b.

If the TCP of the endoscope 152 is located inside the body cavity c, the insertion section 152a is held, extending through the hole b, that is to say, the insertion section 152a has its axis passing through the point-lock position 134, and the TCP of the endoscope 152 is located at the position designated by the signals output from the force sensors 153a and 153b, and the slave manipulator 151 is rotated around its axis by the angle represented by the signals generated by the force sensors 153a and 153b.

With the seventh embodiment it is possible to move the slave manipulator 151 to enable the distal portion 152a of the endoscope 152 to have its axis passing through the point-lock position 134, even if the manipulator 151 fails to be positioned or oriented so as to hold the endoscope 152 at an appropriate position with respect to the hole b, in accordance with the signals generated by the force sensors 153a and 153b. As a result, the insertion section 152a of the endoscope 152 does not apply an excessive force to the body wall a.

Since the slave manipulator 151 is moved in the same way as the surgeon has moved the slave manipulator 151, while holding the handles 154 and thus operating force sensors 153a and 153b mounted on the handles 154, the distal end of the endoscope 152 can be moved to any desired position within the body cavity c.

Figure 19A:
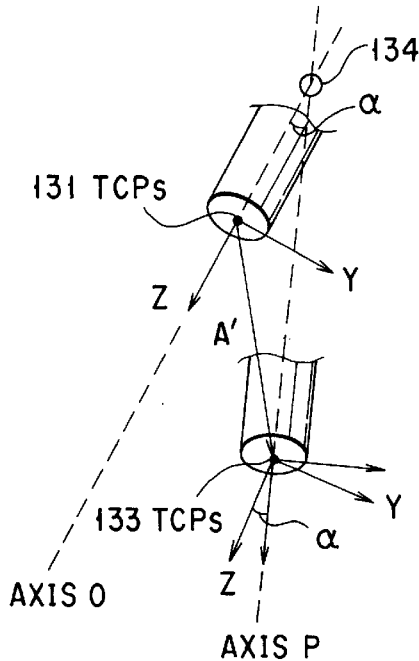
FIGS. 19A and 19B are diagrams for explaining the operation of the surgical manipulator system shown in FIG. 18.

A surgical manipulator system according to the eighth embodiment of this invention will be described, with reference to FIG. 18 and FIGS. 19A and 19B. The seventh embodiment is characterized by the use of a three-dimensional position sensor. The position sensor serves to determine a position and an orientation the slave manipulator may assume so that the medical instrument held by the slave manipulator may not apply an excessive force at the hole which is cut in a body wall and through which the instrument is partly inserted into the body cavity.

Figure 18:
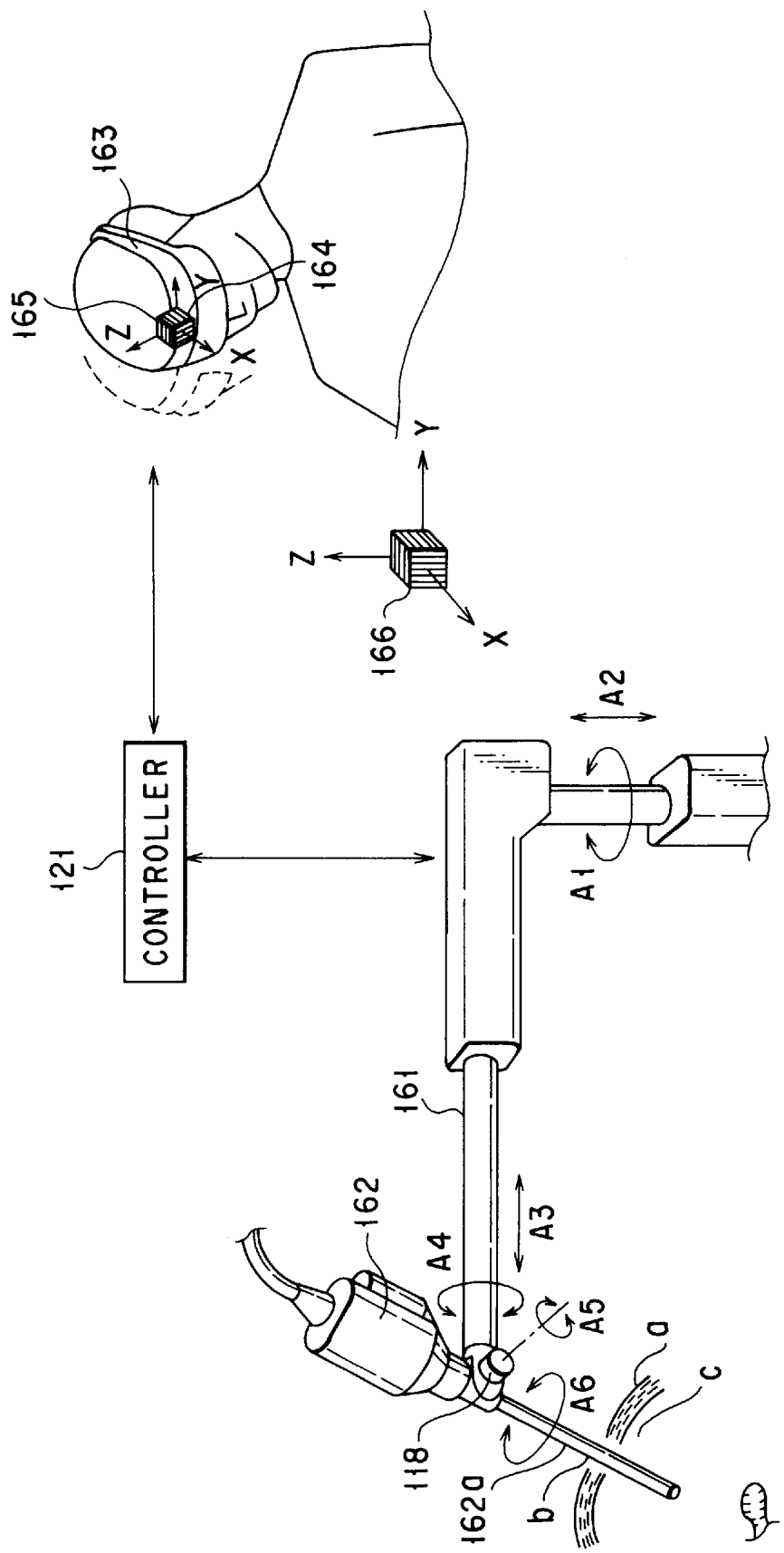
FIG. 18 is a diagram showing a surgical manipulator system which is an eighth embodiment of the present invention.

As shown in FIG. 18, this surgical manipulator system comprises a controller 121, a slave manipulator 161, a three-dimensional endoscope 162, a HMD 163, and a three-dimensional position sensor 164. The endoscope 162 is attached to the manipulator 161 and may have its insertion section 162a inserted into the body cavity c of a patient through a hole b cut in the body wall a of the patient. The position detector 164 comprises a magnetism-detecting section 165 and a magnetism-generating section 166. The detecting section 165 is mounted on an HMD 163 which a surgeon wears while performing a surgery by operating the system. The position the magnetism-generating section 166 assumes with respect to the detecting section 165 is detected to determine the motion of the head of the surgeon wearing the HMD 163.

The slave manipulator 161 and the three-dimensional position sensor 164 are connected to the controller 121. The controller 121 is designed to control the slave manipulator 161 such that the manipulator 161 assumes the position and orientation determined from signals generated by the detecting section 165.

The slave manipulator 161 comprises a plurality of arms and has actuators (not shown) such as electric motors, encoders 118, and reduction mechanisms (not shown). One actuator, one encoder, and one reduction mechanism are provided for each of the arms of the slave manipulator 161. Each section 165, 166 of the sensor 164 has three electromagnetic coils whose axes intersect at right angles. As mentioned above, the section 165 is mounted on the HMD 163. The sensor 164 can detect three position vectors and three orientations which pertain to the slave manipulator 161, from the changes in mutual inductance of the detecting section 165 and the magnetism-generating section 166.

The three-dimensional position sensor 164 may be replaced by, for example, an ultrasonic sensor, an optical sensor, a gyromagnetic sensor or an acceleration sensor. Still alternatively, the position sensor 164 may be replaced by a vision-line sensor which can detect the optical axes of the surgeon's eyes.

As shown in FIG. 18, the endoscope 162 having a three-dimensional scope is attached to the slave manipulator 161 and used as a medical instrument. Instead of the endoscope 162, a medical instrument of any other type that comprises an endoscope and an insertion section or by a medical instrument which comprises neither an endoscope nor an insertion section can be used. The endoscope 162 incorporates a bending mechanism (not shown) in its distal portion. Nonetheless, the endoscope 162 may be a rigid scope which has no bending mechanism at all. The controller 121 is identical to the control section shown in FIG. 10 and which will not be described in detail.

The operation of the surgical manipulator system which is shown in FIG. 18 and which is the eighth embodiment of the invention will now be explained.

Figure 19B:
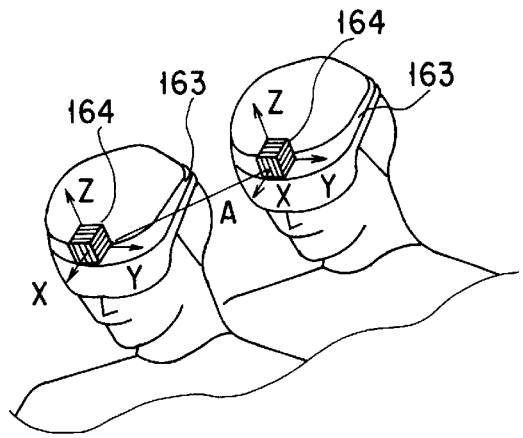

Assume that the surgeon wearing the HMD 163 moves his or her head as illustrated in FIG. 19B, and that the detecting section 165 of the sensor 164 is set at the position represented by a coordinate transform matrix A. The controller 121 easily determines the position and orientation of each element of the matrix A from the Eulerian angles (roll, pitch and yaw) from the signals which are supplied from the detecting section 165 to the controller 121 and which represent the position (X,Y,Z) and inclination of the surgeon's head.

Namely, the controller 121 obtains a coordinate transform matrix A' (or the vector connecting the TCPs 131 and TCPs 133 shown in FIG. 19A) which is identical to the coordinate transform matrix A representing the desired position of the slave manipulator 161. Further, the controller 121 defines an axis P which is the line passing the TCPs 133 and the point-lock position 134, and also an axis O which is the line passing the TCPs 131 and the point-lock position 134. Next, the controller 121 obtains an angle α defined by axes O and P and a vector Q perpendicular to the plane defined by the axes O and P. The controller 121 controls the slave manipulator 161 to the TCPs 133, while rotating the manipulator 161 by the angle α around the vector Q. The controller 121 repeatedly controls the slave manipulator 161 in point-locked mode in this way, at regular intervals, whereby the surgical manipulator system is operated in master-slave mode, while the slave manipulator 161 remains point-locked.

As in the sixth embodiment, a non-response region is therefore provided near the hole b, allowing the slave manipulator 161 (and hence the endoscope 162) to move smoothly as the manipulator 151 is inserted into or pulled from the body cavity through the hole b. The insertion section 162a of the endoscope 162 held by the slave manipulator 161 may not apply an excessive force at the hole which is cut in a body wall and through which the instrument is partly inserted into the body cavity.

In the eighth embodiment, the slave manipulator 161 is moved in the same way as the surgeon moves his or her head since the detecting section 165 is mounted on the HMD 163 which the surgeon wears. The distal end of the endoscope 162 held by the slave manipulator 161 is thereby moved to the desired position in the body cavity b. Thus, the surgeon can see the image of the interior of the body cavity c while carrying out the surgery, as if he or she were in the body cavity c.

A surgical manipulator system according to the ninth embodiment of the invention will be described, with reference to FIG. 20, FIGS. 21A to 21C and FIG. 22. The ninth embodiment is characterized by the use of force sensors which are mounted on slave manipulator. The force sensors serve to determine a position and an orientation the slave manipulator may take so that the medical instrument held by the slave manipulator may be partly inserted straight into a body cavity and its distal end may be guided to an object to be examined and treated.

Figure 20:
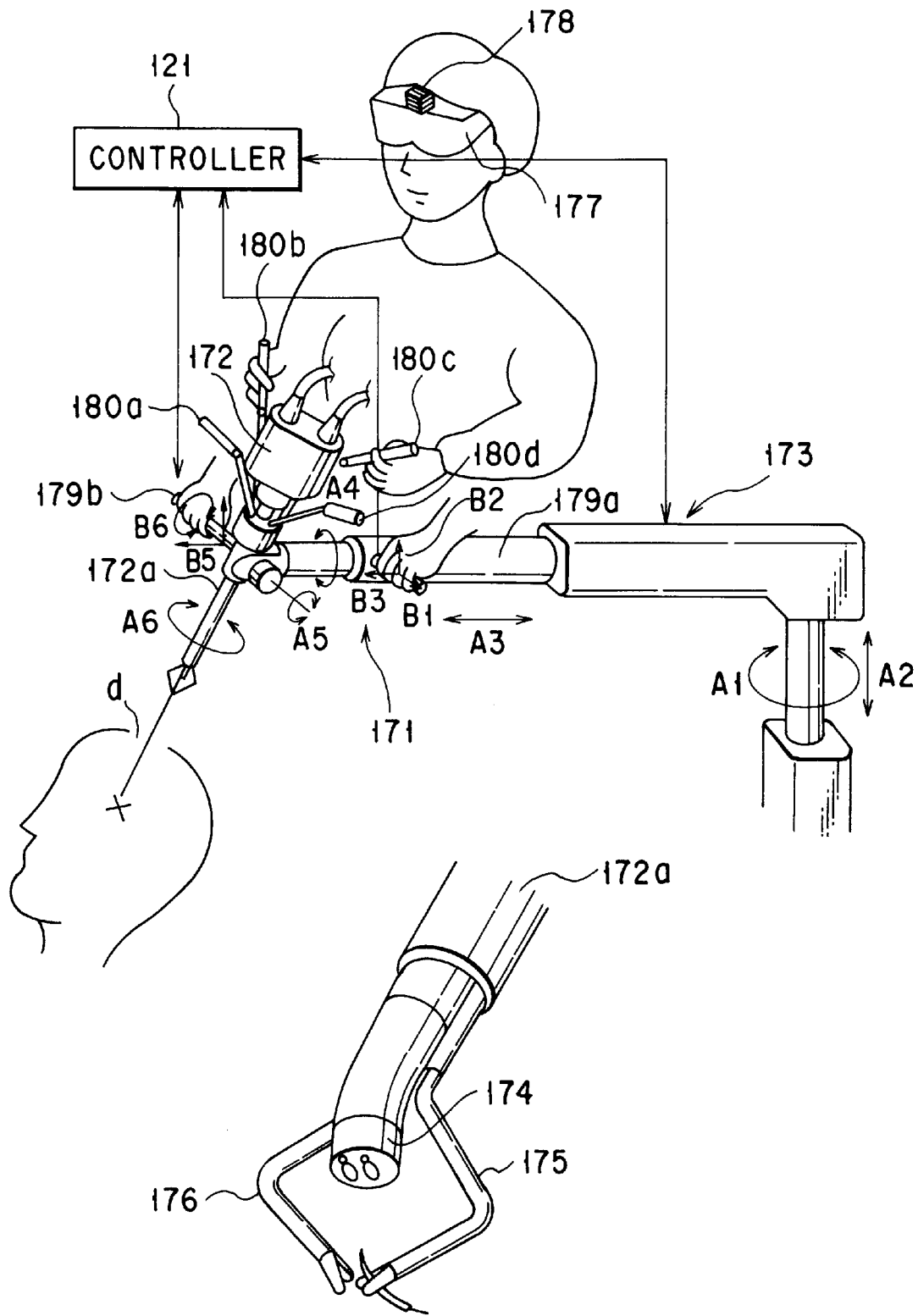
FIG. 20 is a diagram showing a surgical manipulator system which is a ninth embodiment of the present invention.

As shown in FIG. 20, the surgical manipulator system according to the ninth embodiment comprises a controller 121, a slave manipulator 171 and a HMD 177. The slave manipulator 171 is electrically connected to the controller 121 and comprises a medical device 172 and a robot 173 for holding the device 172. The medical device 172 has an insertion section 172a which can be inserted into a cavity in the patient's head d. The robot 173 has a plurality of arms. Hence, it has many degrees of freedom, capable of moving linearly and rotating the medical instrument 172. Formed integral with the distal end of the insertion section 172a of the device 172 are an endoscope 174 and a pair of medical instruments 175 an 176. A three-dimensional scope is incorporated in the distal portion of the endoscope 174. The distal portion of the endoscope 174 can be bent in various directions. The distal portions of the instruments 175 and 176 can be bent in various directions, too. A three-dimensional position sensor 178 is connected to the HMD 177, which a surgeon wears while carrying out surgery by using the system. The three-dimensional position sensor 178 is electrically connected to the controller 121.

Two force sensors 179a and 179b are connected to the slave manipulator 171. Both force sensors 179a and 179b are electrically connected to the controller 121. The sensor 179a contains a strain gauge which can detect three vectors indicating the directions in which the surgeon applies forces to the sensor 179a. Similarly, the sensor 179b contains a strain gauge which can detect two vectors indicating the directions in which the surgeon applies forces to the sensor 179b and one direction in which surgeon rotates the sensor 179b. The controller 121 is designed to control the slave manipulator 171 such that it takes the position and orientation determined from signals generated by the force sensors 179a and 179b and to control the endoscope 174 such that it takes orientation determined from signals generated by the sensor 178.

The medical instruments 175 and 176 are mechanically controlled as the surgeon operates operation sections 180a, 180b, 180c and 180d which are connected to the slave manipulator 171.

As indicated above, the endoscope 174 and the instruments 175 and 176 are formed integral with the insertion section 172a of the medical device 172. Instead, only the endoscope 174 may be formed integral wit the insertion section 172a, or only the medical instruments 175 and 176 may be formed integral therewith. The endoscope 174 incorporates a bending mechanism (not shown) in its distal portion. Nonetheless, the endoscope 174 may be a rigid scope which has no bending mechanism at all. The controller 121 is identical to the control section shown in FIG. 10 and which will not be described in detail.

In neurosurgery, the point-lock position of the instrument used is present within the patient's head d. Before the surgery the surgeon needs to know the point-lock position by means of an image forming apparatus such as a CT scanner. He or she may input position data into the controller 121 by operating an input device (not shown), thereby to confirm the positional relation between the point-lock position and the slave manipulator 171.

The operation of the surgical manipulator system according to the ninth embodiment will be explained.

Figure 21A:
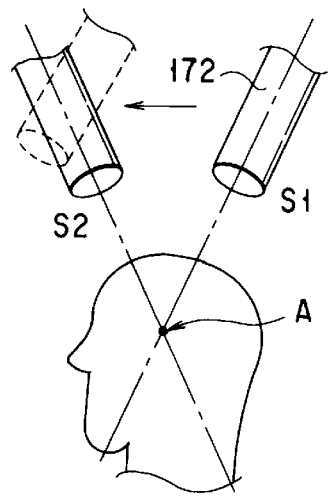
FIGS. 21A to 21C are diagrams for explaining the operation of the system shown in FIG. 20.

Assume the surgeon operates the slave manipulator 171, thereby moving the force sensor 179a forwards and, thus, extending the arm A3 of the robot 173, in order to move the medical device 172 horizontally from position S1 to position S2 as shown in FIG. 21A. As a result, a force is applied to the force sensor 179a in the horizontal direction of arrow B3. If the system is not set in the point-locked mode, the distal portion of the device 172 is oriented as indicated by the broken lines in FIG. 21A. If the system is set in the point-locked mode, the distal portion of the device 172 is oriented as indicated by solid lines in FIG. 21A so that the axis of the medical device 172 may be aligned with the point-lock position A.

Figure 21B:
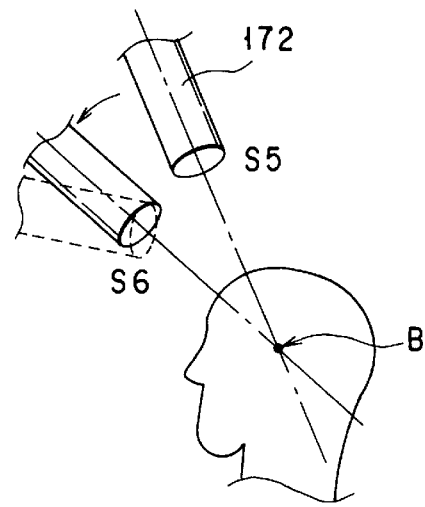
Figure 21C:
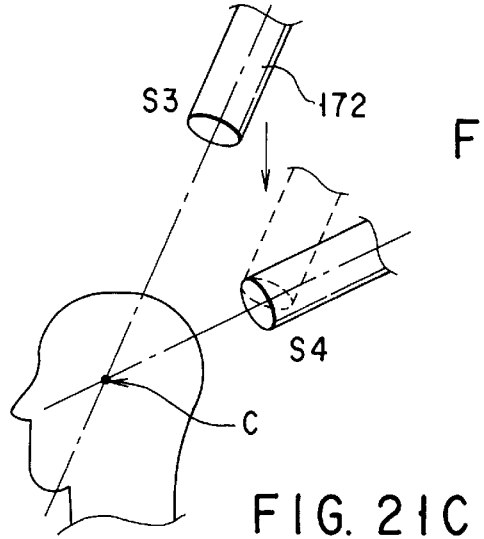

The surgeon may operate the slave manipulator 171, moving the force sensor 179a downwards and, thus, pushing down the arm A2 of the robot 173, in order to move the medical device 172 downwards from position S3 to position S4 as illustrated in FIG. 21C. In this case, a force is applied to the force sensor 179a in the reverse direction against arrow B2 shown in FIG. 20. If the system is not set in the point-locked mode, the distal portion of the device 172 is oriented as shown by the broken lines in FIG. 21C. If the system is set in the point-locked mode, the distal portion of the device 172 is oriented as indicated by solid lines in FIG. 21C so that the axis of the medical device 172 may be aligned with the point-lock position C.

The surgeon may rotate the force sensor 179b in the direction of arrow B6 shown in FIG. 20, in order to rotate the medical device 172 from position S5 to position S6 as depicted in FIG. 21b. If the system is not set in the point-locked mode, the distal portion of the device 172 is oriented as indicated by the broken lines in FIG. 21B. If the system is set in the point-locked mode, the distal portion of the device 172 is oriented as indicated by solid lines in FIG. 21B so that the axis of the medical device 172 may be aligned with the point-lock position B.

In neurosurgery, the insertion section 172a must be prevented from passing through the point-lock position. Should the distal end of the section 172a reach the point-lock position, there will exist a singular point as in the sixth embodiment. In this case, a non-response region is provided near the point-lock position, and the controller 121 controls the slave manipulator 171, moving the insertion section 172a near the non-response region with its inclination not changed.

Figure 22:
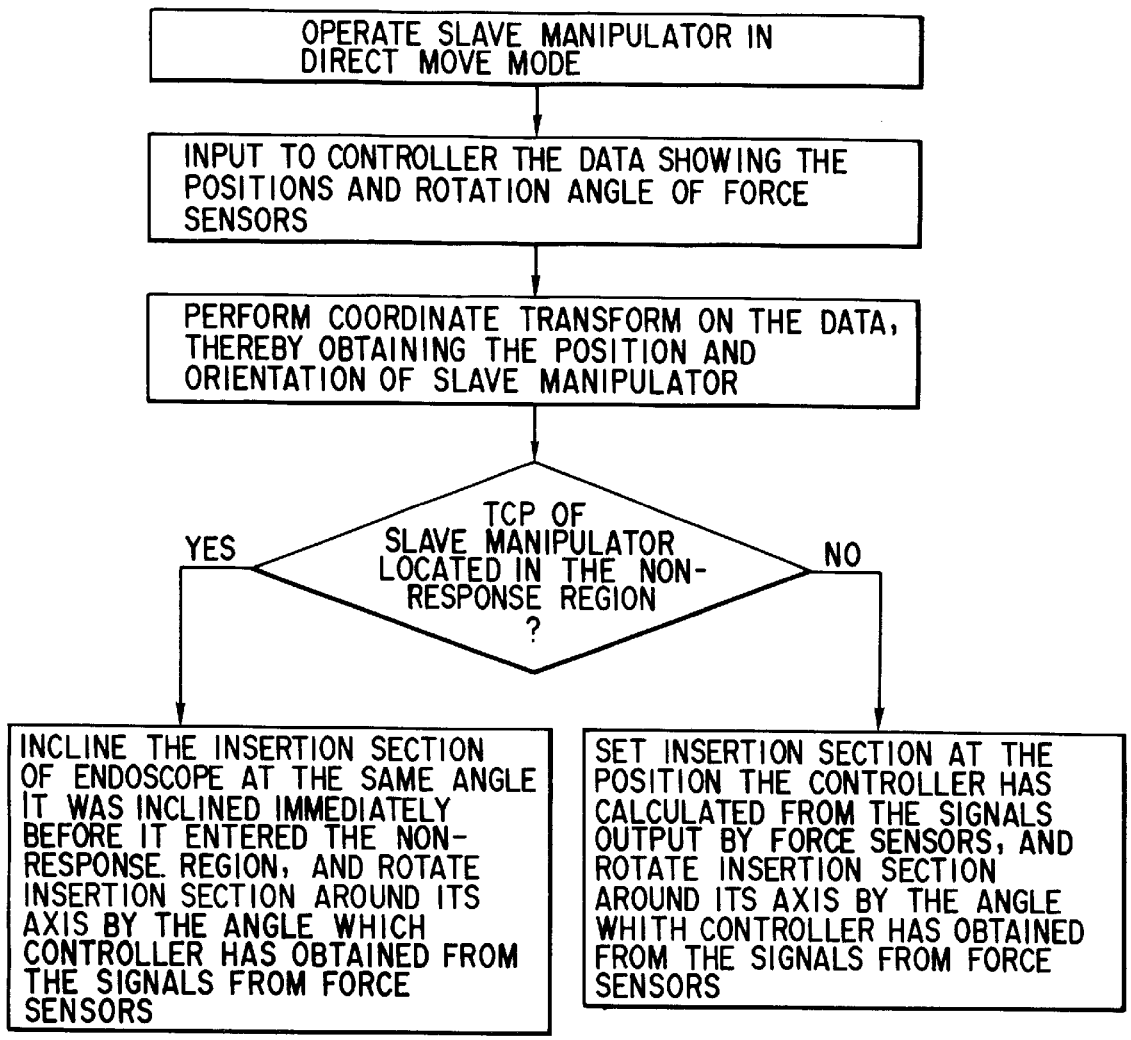
FIG. 22 is a flow chart for explaining the operation of the surgical manipulator system illustrated in FIG. 20.

FIG. 22 is a flow chart for explaining how the surgical manipulator system of FIG. 20 is operated. First, the surgeon operates the slave manipulator 171 in direct move mode, whereby the data representing the positions of the force sensors 179a and 179b and the angles of rotation thereof is input the controller 121. The controller 121 performs a coordinate transform on the input data, thereby obtaining the position and orientation of the slave manipulator 171. Then, the controller 121 determines whether or not the TCP of the manipulator 171 is located in the non-response region.

If the TCP of the manipulator 171 is located within the non-response region, the insertion section 172a is inclined at the same angle it was inclined immediately before it entered the non-response region, and is rotated around its axis by the angle the controller 121 obtained from the signals output by the force sensors 179a and 179b. If the TCP of the manipulator 171 is located outside the non-response region, the medical device 172 is set at the position the controller 121 has calculated from the signals output by the force sensors 179a and 179b, and is rotated around its axis by the angle the controller 121 obtained from the signals output by the force sensors 179a and 179b.

With the ninth embodiment described above, it is possible for the surgeon to operate the slave manipulator 171 even if the insertion section 172a of the medical instrument 172 held by the manipulator 171 fails to have its axis aligned with the lock-point position located in the patient's head d. In addition, since the slave manipulator 171 is operated in the same way as the surgeon moves the force sensors 172a and 172b, the surgeon can operate the medical device 172 in the patient's head d as he or she desires. Moreover, the endoscope 174 secured to the slave manipulator 171 is moved in the patient's head d to a desired position as the surgeon moves his or her head and, thus, the three-dimensional position sensor 178 connected to the HMD 177 which he or she wears. Thus, while carrying out the surgery, the surgeon can see the image of the interior of the patient's head d as if he or she were in the head d.

Figure 23A:
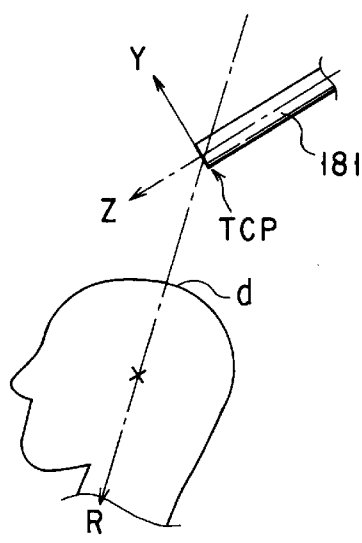
FIGS. 23A to 23C are diagrams for explaining the operation of a surgical manipulator system according to a tenth embodiment of the invention.
Figure 23B:
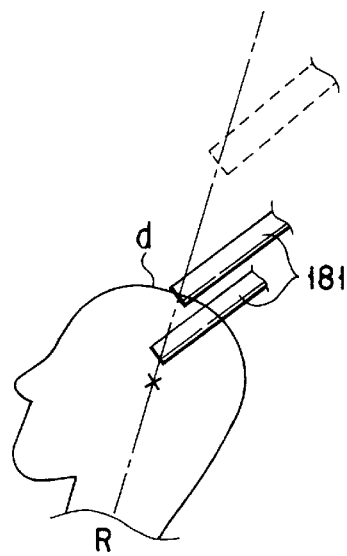
Figure 23C:
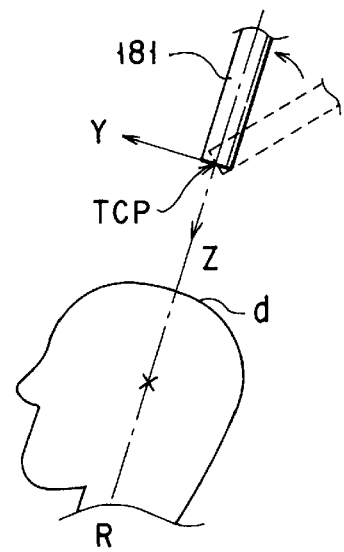

FIGS. 23A to 23C are diagrams for explaining the operation of a surgical manipulator system according to the tenth embodiment of the invention. This embodiment is characterized in that, as the master manipulator is operated, the slave manipulator is positioned and oriented to prevent the medical device it holds from applying an excessive force at the hole which is cut in a body wall and through which the instrument is partly inserted into the body cavity.

To set a medical instrument 181 at an appropriate position within a patient's head d as in the case of the ninth embodiment, the surgeon first sets the system into point-locked mode and the instrument. Unless the axis of the medical instrument 181 is aligned with the point-lock position in the patient's head d, he or she cannot insert the instrument 181 into the head d. To enable the surgeon to insert the instrument 181, the orientation of the distal portion of the instrument 181 is changed in the present embodiment as will be explained below. This is a third control mode.

FIG. 23A illustrates the position relation between the distal portion of the medical instrument 181 and the patient's head d. If the instrument 181 is inserted into the head d unless its orientation is changed, it will abut on the head d as shown in FIG. 23B, inevitably inflicting injury. To insert the instrument 181 into the head d without inflicting injury, the orientation of the distal portion of the instrument 181 is changed in the present embodiment—in the following way.

The controller 121 of this surgical manipulator system, which is identical to the control section shown in FIG. 10, determines the orientation which the distal portion of the instrument 181 assumes at present with respect to the line R connecting a desired TCP in the patient's head d and the actual TCP of the instrument 181. The controller 121 then controls the slave manipulator 171, orienting the distal portion of the instrument 181 into alignment with the line R as is illustrated in FIG. 23C. This done, the medical instrument 181 is gradually inserted into the patient's head d by means of point-lock control.

With the tenth embodiment it is possible to align the surgeon with the line connecting a desired TCP located in the patient's head d and the actual TCP of the instrument 181. As a result, it is easy to insert the instrument 181 into the patient's head d.

Figure 24:
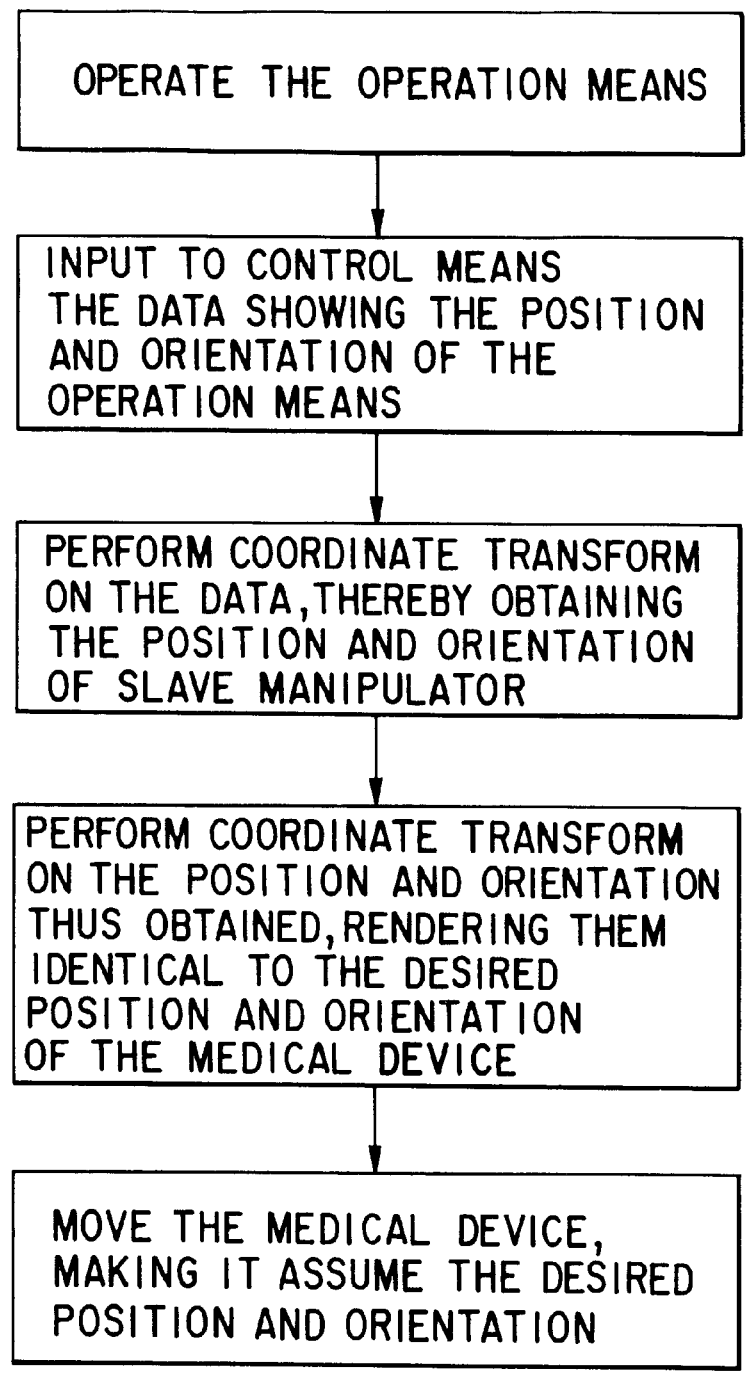
FIG. 24 is a flow chart for explaining the operation of a surgical manipulator system which is an eleventh embodiment of the present invention.

FIG. 24 is a flow chart for explaining the operation of a surgical manipulator system which is the eleventh embodiment of the present invention. This system comprises operation means, control means, and a slave manipulator. First, the surgeon operates the operation means, thereby inputting to the control means the data representing the position and orientation of the operation means. Then, the control means performs coordinate transform on the input data, thereby obtaining the position and orientation which the medical device held by the slave manipulator should take. The control means performs coordinate transform on the position and orientation thus obtained, rendering them identical to the desired position and orientation of the medical device.

FIG. 25 is a flow chart for explaining the operation of a surgical manipulator system which is the twelfth embodiment of the invention. The twelfth embodiment comprises a master manipulator, a slave manipulator, a controller and a medical device. The medical device is attached to the distal end of the slave manipulator. How to operate this system will be explained below.

First, a surgeon sets the system into direct move mode, and moves the slave manipulator, setting the distal portion of the medical device at the hole cut in the body wall of a patient. Thereby, the data representing the position of the hole is input to the controller. The controller performs coordinate transform on the input data, controlling the slave manipulator and changing the orientation of the distal portion of the device so that the device may be inserted into the body cavity through the hole. Thereafter, the surgeon operates the master manipulator, changing the position of the distal end of the master manipulator and rotating the master manipulator. The data representing the position and rotation angle of the master manipulator is input to the controller.

The controller performs coordinate transform on the input data, obtaining the position and orientation which the slave manipulator should have to guide the medical device smoothly into the body cavity through the hole cut in the body wall. Further, the controller determines whether or not the distal end of the device is located near the hole. If the distal end of the device is present near the hole, the insertion section of the device is rotated by the same angle the master manipulator has been rotated and is then inserted into the body cavity, with its inclination angle not changed. If the distal end of the medical device is not located near the hole, the insertion section of the device is inserted into the body cavity through the hole, and the distal end thereof (i.e., the TCP of the slave manipulator) is set at the position obtained by operating the master manipulator. Further, the insertion section of the device is rotated by the same angle that the master manipulator has been rotated.

As described above, in the sixth to twelfth embodiments above, the controller 121 can operate in three modes to control the slave manipulator in various ways (e.g., point locking and the like). The operating modes of the controller 121 can be switched, from one to another, by operating the keyboard 13 of the controller 121. In the first operating mode, the controller 121 controls the slave manipulator or the medical device, or both, such that the axis of the device is always aligned with a point-lock position. In the second operating mode, the controller 121 controls the slave manipulator or the medical device, or both, such that the medical device remains inclined during the surgery, at the same angle as it was inclined immediately before the insertion of its distal portion. In the third operating mode, the controller 121 controls the slave manipulator or the medical device, or both, such that the axis of the device is always aligned with a point-lock position, while its distal portion is able to move in a straight line.

In this case, the controller 121 operates in the first mode after a distal portion of the medical device has been inserted through the hole into the body cavity and operates in the second mode from the time the distal portion of the medical device is located near the hole to the time the distal portion of the medical device reaches a desirable position in the body cavity. In the other case, the controller 121 operates in the first mode throughout the use of the system.

What is claimed is:

1. A surgical manipulator system comprising:

a slave manipulator which is movable to be positioned in a surgery region;

a medical device having a distal end, said medical device being held by the slave manipulator and being movable into a body cavity;

operation means for operating the slave manipulator and the medical device, said operation means being positioned within a movement region in which a surgeon can freely operate; and control means for calculating conditions in which said slave manipulator needs to be moved in response to a movement of said operation means, said control means being operable in at least a first control mode in which at least one of said slave manipulator and said medical device is moved in the conditions calculated and in association with the movement of the operation means such that a longitudinal axis of said medical device always passes one fixed point in space even before the medical device is inserted into a body cavity, said fixed point being set before a surgical operation by reading coordinates of the fixed point in space.

2. The system according to claim 1, wherein said control means determines a position of the distal end of said medical device.

3. The system according to claim 2, wherein said fixed point in space is located at a hole cut in a body wall through which said medical device is to be inserted into the body cavity.

4. The system according to claim 3, wherein said control means operates said slave manipulator in the first control mode after a distal portion of said medical device has been inserted through the hole into the body cavity.

5. The system according to claim 3, wherein said control means continuously operates said slave manipulator in the first control mode throughout the use of the system.

6. The system according to claim 3, wherein said control means is operable in a second control mode in which at least one of said slave manipulator and said medical device is moved in the conditions calculated, such that the longitudinal axis of said medical device is kept inclined at a same angle as immediately before a distal portion of said medical device is inserted into the body cavity.

7. The system according to claim 6, wherein said control means operates said slave manipulator in said second control mode from a time the distal portion of said medical device is located near the hole to a time the distal portion of said medical device reaches a given position in the body cavity.

8. The system according to claim 2, wherein said control means is operable in a third control mode in which at least one of said slave manipulator and said medical device is moved in the conditions calculated, such that the longitudinal axis of the medical device passes through said fixed point in space while enabling the distal end of said medical device to move in a straight line.

9. The system according to claim 1, wherein said fixed point in space is located in the body cavity.

10. The system according to claim 9, wherein said control means operates in said first mode throughout the use of the system.

11. The system according to claim 1, wherein said medical device comprises an endoscope.

12. The system according to claim 1, wherein said medical device comprises a medical instrument.

13. The system according to claim 12, wherein said medical instrument includes an observation unit.

14. The system according to claim 1, wherein said operation means comprises a master manipulator.

15. The system according to claim 1, wherein said operation means comprises a force sensor mounted on said slave manipulator.

16. The system according to claim 1, further comprising a sensor which detects at least one of a position and an orientation of said slave manipulator to be used for calculation by said control means.

17. The system according to claim 1, further comprising:
 a scope insertable into the body cavity for enabling observation inside the body cavity;
 a scope slave manipulator coupled to said scope for controlling movement of said scope; and
 a master scope manipulator for controlling said scope slave manipulator to move said scope independently of the movement of said medical device.

18. The system according to claim 17, wherein said master scope manipulator comprises a head mount display for enabling observation inside the body cavity.

19. The system according to claim 18, wherein said master scope manipulator includes means for controlling said scope slave manipulator to move said scope responsive to a movement of a head of the surgeon.

20. A surgical manipulator system comprising:
 a slave manipulator movable to be positioned in a surgery region;
 a medical device having a distal end, said medical device being held by the slave manipulator and being movable into a body cavity;
 operation means for operating the slave manipulator and the medical device, said operation means being positioned within a movement region in which a surgeon can freely operate;
 control means for reading coordinates of a fixed point in space, and setting the fixed point by calculation before a surgical operation, and for calculating conditions in which said slave manipulator needs to be moved in response to a movement of said operation means; and
 mode-switching means for switching an operating mode of said control means;
 wherein said control means is operable in: (i) a first control mode in which at least one of said slave manipulator and said medical device is moved in the conditions calculated and in association with the movement of the operation means such that a longitudinal axis of said medical device always passes one fixed point in space even before the medical device is inserted into a body cavity, said fixed point being set before a surgical operation by reading coordinates of the fixed point in space, (ii) a second control mode in which at least one of said slave manipulator and said medical device is moved in the conditions calculated, such that the longitudinal axis of said medical device is kept inclined at a same angle as immediately before said distal end of said medical device is inserted into the body cavity, when said fixed point in space is located at a hole cut in a body wall through which said medical device is to be inserted into the body cavity, and (iii) a third control mode in which at least one of said slave manipulator and said medical device is moved in the conditions calculated, such that the longitudinal axis of said medical device passes through said fixed point in space while enabling the distal end of said medical device to move in a straight line.

21. A surgical manipulator system comprising:
 a slave manipulator which is movable to be positioned in a surgery region;
 a medical device which is held by the slave manipulator and which is movable into a body cavity;
 operation means for operating the slave manipulator and the medical device, said operation means being positioned within a movement region in which a surgeon can freely operate;
 control means for calculating conditions in which said slave manipulator needs to be moved in response to a movement of said operation means, said control means being operable in at least a first control mode in which at least one of said slave manipulator and said medical device is moved in the conditions calculated and in association with the movement of the operation means such that a longitudinal axis of said medical device always passes one fixed point in space even before the medical device is inserted into a body cavity, said fixed point being set before a surgical operation by reading coordinates of the fixed point in space; and
 parameter changing means for changing a control parameter required for controlling at least one of said slave manipulator and said medical device.

22. The system according to claim 21, wherein said control parameter is a ratio of a distance said slave manipulator is moved to a distance said operation means is moved.

23. The system according to claim 21, wherein said control parameter is a distance less than a shortest distance by which said slave manipulator is moved when said operation means is operated.

24. The system according to claim 21, wherein said control means restricts motion of said slave manipulator when said operation means is moved for a distance longer than a predetermined value.

25. The system according to claim 24, further comprising an alarm unit which generates an alarm when said operation means is moved a distance longer than a predetermined value.

26. The system according to claim 21, wherein said control means is operable in a second control mode in which at least one of said slave manipulator and said medical device is moved in the conditions calculated, such that the longitudinal axis of said medical device is kept inclined at a same angle as immediately before a distal portion of said medical device is inserted into the body cavity, when said fixed point in space is located at a hole cut in a body wall through which said medical device is to be inserted into the body cavity.

27. The system according to claim 26, wherein said parameter changing means comprises mode switching means for switching the operation mode of said control means.

28. The system according to claim 21, wherein said parameter changing means comprises switching means for changing the control parameter.

29. The system according to claim 28, wherein said switching means comprises a foot switch.

30. The system according to claim 28, wherein said switching means comprises a switch located near said operation means.

31. The system according to claim 21, wherein said medical device comprises an endoscope.

32. The system according to claim 21, wherein said medical device comprises a medical instrument.

33. The system according to claim 32, wherein said medical instrument includes an observation unit.

34. The system according to claim 21, wherein said operation means comprises a master manipulator.

35. The system according to claim 21, wherein said operation means comprises a force sensor mounted on said slave manipulator.

36. The system according to claim 21, further comprising a sensor which detects at least one of a position and an orientation of said slave manipulator to be used for calculation by said control means.

* * * * *